United States Patent [19]

Snook

[11] Patent Number: 5,512,965
[45] Date of Patent: Apr. 30, 1996

[54] OPHTHALMIC INSTRUMENT AND METHOD OF MAKING OPHTHALMIC DETERMINATIONS USING SCHEIMPFLUG CORRECTIONS

[75] Inventor: Richard K. Snook, Tucson, Ariz.

[73] Assignee: Orbtek, Inc., Salt Lake City, Utah

[21] Appl. No.: 329,238

[22] Filed: Oct. 26, 1994

Related U.S. Application Data

[63] Continuation-in-part of Ser. No. 80,497, Jun. 24, 1993.
[51] Int. Cl.[6] .................................................. A61B 3/10
[52] U.S. Cl. ............................ 351/205; 351/212; 351/214; 351/211
[58] Field of Search ................................ 351/205, 211, 351/212, 214, 221

[56] References Cited

U.S. PATENT DOCUMENTS

| | | | |
|---|---|---|---|
| 4,523,821 | 6/1985 | Lang et al. | 351/214 |
| 4,711,541 | 12/1987 | Yoshino et al. | 351/214 |
| 5,341,180 | 8/1994 | Isogai et al. | 351/214 |

Primary Examiner—William L. Sikes
Assistant Examiner—Huy Mai
Attorney, Agent, or Firm—Robert J. Schaap

[57] ABSTRACT

An ophthalmic instrument, in the nature of a pachymeter or densitometer, and which is used for ascertaining the thickness and relative optical density of the cornea of the eye on a real time basis. The instrument comprises a television camera and a multiple Scheimpflug corrected slit projector and an associated processing and display system. A number of digitally encoded television images of the optical section of the cornea are subjected to digital analysis. A density map may be constructed from the data derived in the digital analysis and produced for display either by a printer or display member. The display may be a three-dimensional plot of the frontal surface shape, local thickness, posterior surface contour and optical density of the cornea. A method of using the ophthalmic instrument and of making ophthalmic determinations is also disclosed.

25 Claims, 9 Drawing Sheets

Cross section, Right eye (top view)

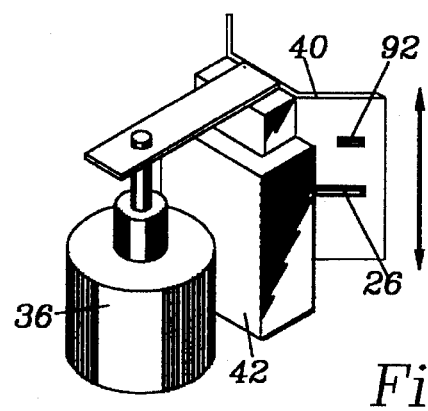
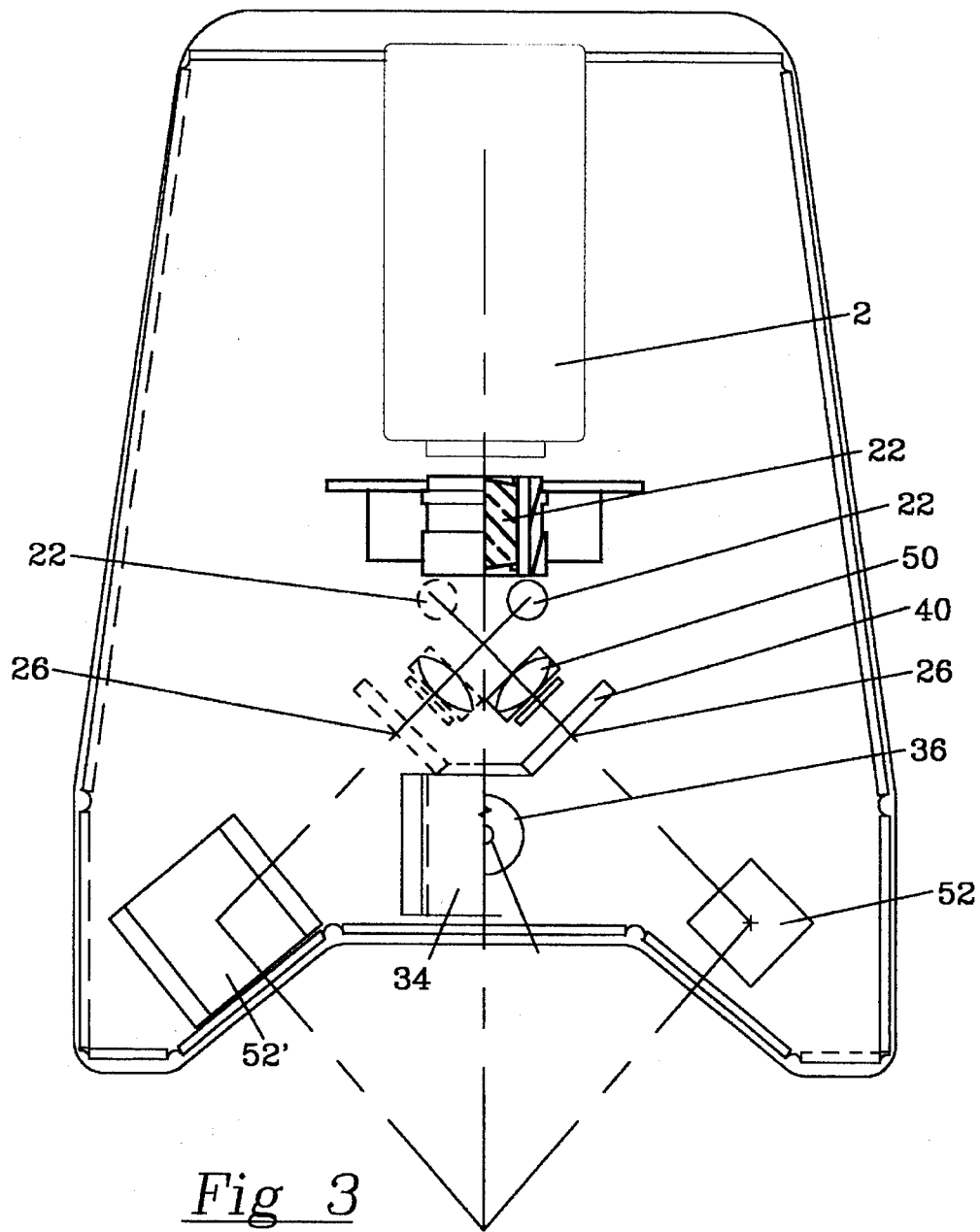
Fig 4
Fig 3

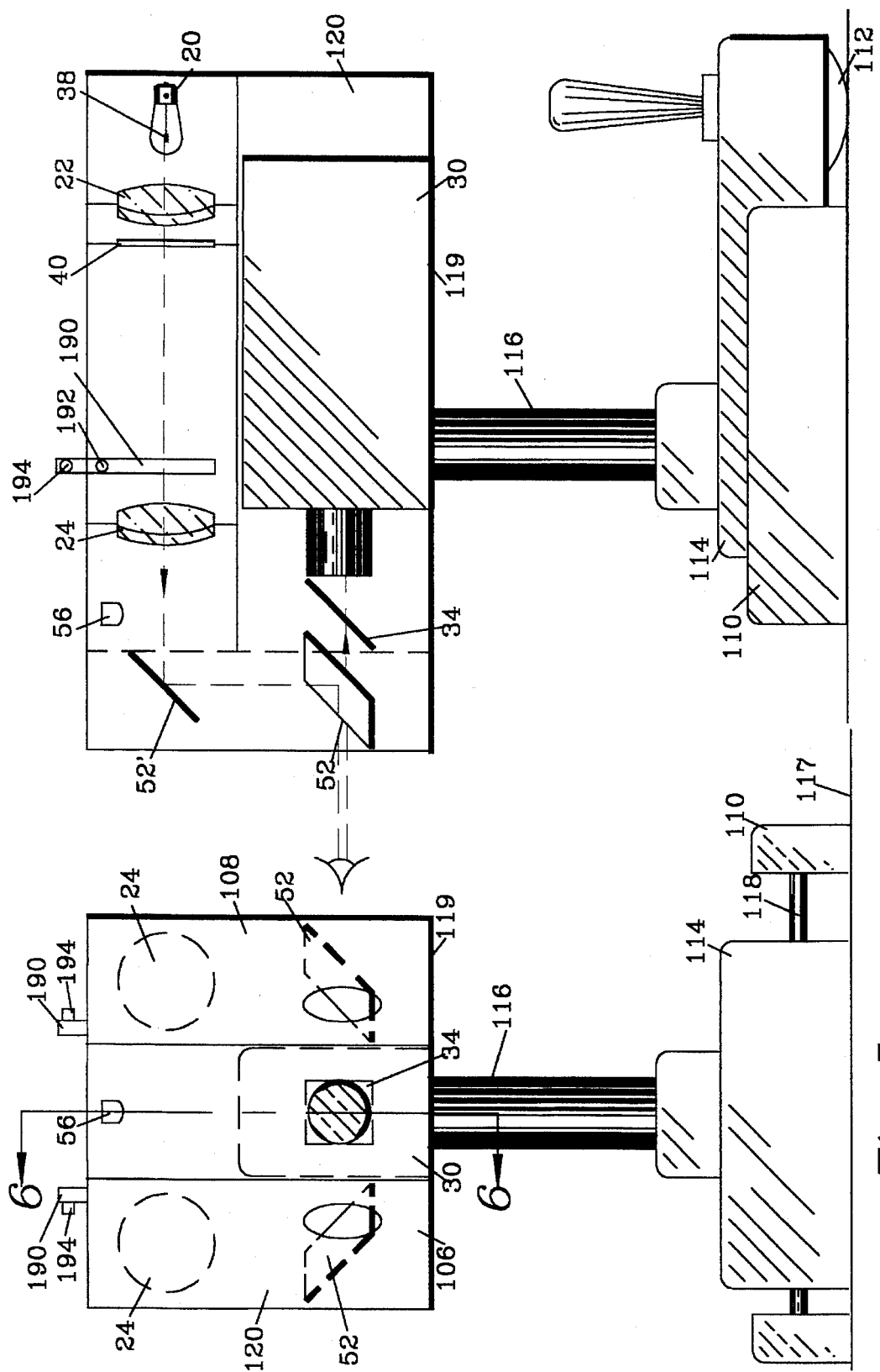

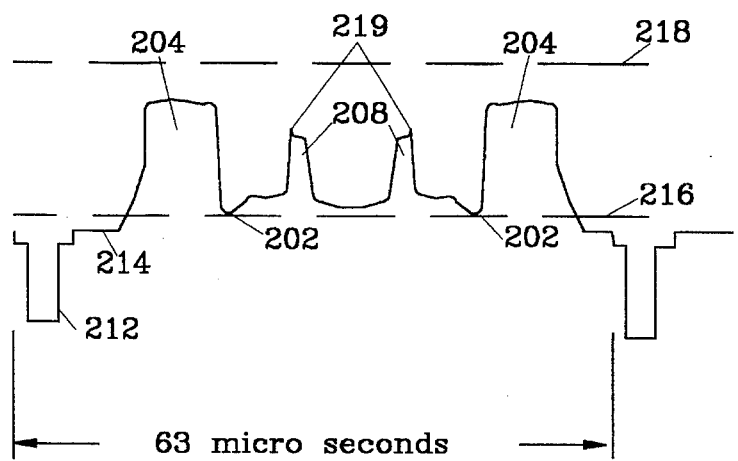
*Fig 21*
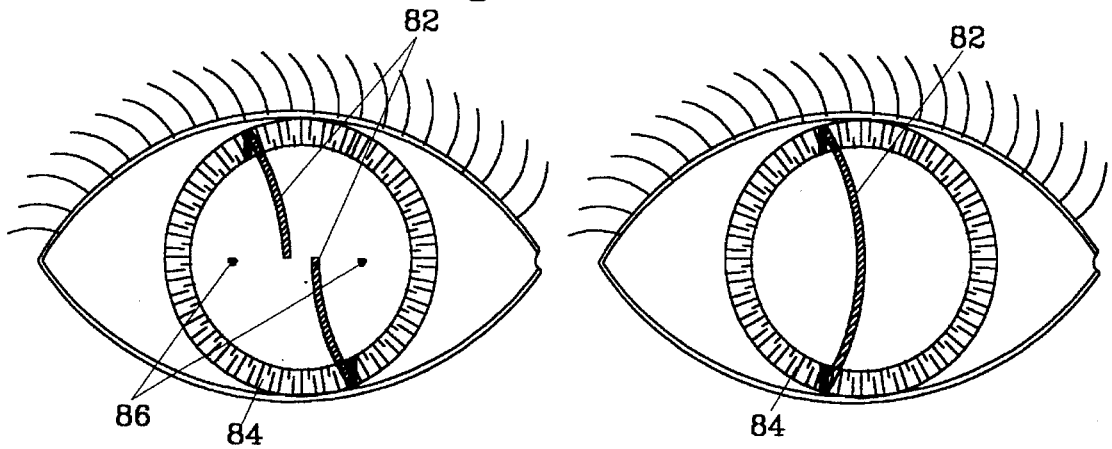
*Fig 9A*           *Fig 9B*

OPHTHALMIC INSTRUMENT AND METHOD OF MAKING OPHTHALMIC DETERMINATIONS USING SCHEIMPFLUG CORRECTIONS

RELATED APPLICATION

This application is a continuation-in-part of my co-pending U.S. patent application Ser. No. 080,497 filed Jun. 24, 1993 and entitled "Ophthalmic Pachymeter And Method Of Making Ophthalmic Determinations."

BACKGROUND OF THIS INVENTION

1. Field of the Invention

This invention relates in general to certain new and useful improvements in ophthalmic instruments for aiding in the determination of physical and optical parameters of the cornea of the eye on a real time basis and more particularly, to an improved ophthalmic instrument of the type which is capable of ascertaining thickness, density and surface contour on a real time basis using a television camera and a multiple Scheimpflug corrected slit projector, as well as associated processing.

2. Brief Description of the Related Art

The measurement of optical density of cataracts has been a subject which is becoming more widely addressed in recent times. One of the recent teachings of cataract optical density measurement is set forth in U.S. Pat. No. 4,863,261 to J. Flammer, "Method and Apparatus for Measuring the Extent of Clouding of the Human Eye." The prior art relating to the measurement of optical density is also exemplified in U.S. Pat. No. 4,019,813 for "Optical Apparatus for Obtaining Measurements of Portions of the Eye."

Planning for anterior segment surgery is also a topic which has received increasing attention in recent years, as, for example, in a paper by Lehrman, et al., "Measurement of Anterior Chamber Diameter" and "Biometry of Anterior Segment by Scheimpflug Slit Lamp Photography", reported in Investigative Ophthalmology and Visual Science, Volume 32, No. 3, March 1991, pages 529–532.

The slit lamp is an instrument employed by many optometrists and ophthalmologists for examination of the anterior portion of the eye. Many different versions of the instrument have been produced over the last century, but all of the slit lamps have three major elements in common and which include a projector for providing a collimated image of an optical slit focused on the eye, a bio-microscope or camera for viewing the image and a mechanical support system. In this slit lamp system, the bio-microscope or camera is designed to view the image formed by the projector and is confocal with the projector. The mechanical support system must be elaborate to at least support the subject and the projector and viewing system. Furthermore, the elements must be positioned relative to one another for appropriate examination of the eye.

Pachymetry attachments are available for the slit lamp to be used in clinical environments. These attachments operate so as to displace half the image by a plane parallel glass block interposed in the viewing path. Rotation of the glass block through a calibrated drum changes the optical offset for half of the image and the user places the front edge of the upper image in contact with the opposing edge in the lower half of the image. The reading in the drum is then recorded as the local corneal thickness. This type of pachymeter can accurately define corneal thickness at an unknown location. However, these modified slit lamp devices are slow, expensive and fragile. Moreover, they are quite difficult to operate, and require substantial training on the part of the operator.

One of the most common corneal thickness measurements used in clinical practice today is that of ultrasound. The A-scan ultra sound probe, much the same as with the optical pachymeter, produces a single-point measurement at an unknown locus of the cornea. In addition, this unknown single point is, in reality, the average thickness of an area of several square millimeters in extent. Because the location of the measurement is not repeatable, the data is variable as well.

One of the principal problems of the prior art systems is that the plots which one generated to provide a cornea mapping were not accurate and more importantly, were not repeatable. Thus, the prior art did not provide the ophthalmic surgeon with the data required for planning radial keratotomy or other refractive surgical processes.

Some of the other deficiencies in the prior art techniques used for determining corneal thickness and mapping is hereinafter described in the following Overview Of The Invention. In this Overview Of The Invention, the prior art is, in some cases, also contrasted with the principles of the present invention in order to more fully show the substantial advantages achieved by the present invention. Also, and to some extent, background theory is set forth in order to more fully aid in the understanding of the present invention.

OBJECTS OF THE INVENTION

It is, therefore, one of the primary objects of the present invention to provide an ophthalmic instrument which is capable of measuring relative optical density and thickness of the cornea of the eye on a real time basis.

It is another object of the present invention to provide an ophthalmic instrument in the nature of a densitometer or a pachymeter and which comprises a television camera, along with a multiple Scheimpflug corrected slit projector.

It is a further object of the present invention to provide an ophthalmic instrument of the type stated which is capable of making digitally encoded television images of an optical section of the cornea into digital equivalent representations for construction of an optical map to display certain physical parameters of the eye.

It is an additional object of the present invention to provide an ophthalmic instrument of the type stated which is capable of producing a map of the cornea of the eye and providing a frontal shape, local thickness, posterior surface contour and optical density.

It is still another object of the present invention to provide an ophthalmic instrument of the type stated which vastly improves upon the field of densitometry and pachymetry as currently practiced in the prior art It is yet a further object of the present invention to provide an ophthalmic instrument of the type stated which can be manufactured at a relatively low cost and which is highly reliable in operation.

It is another salient object of the present invention to provide a method of making ophthalmic determinations, including frontal surface shape, local thickness, posterior surface contour and optical density of the cornea of the eye on a real time basis.

With the above and other objects in view, my invention resides in the novel features of form, construction, arrangement and combination of parts presently described and pointed out in the claims.

BRIEF SUMMARY OF THE INVENTION

The present invention provides both a new system for providing corneal thickness and optical density analysis and an associated method for measuring corneal thickness and optical density. In this case, both the instrument and the method provide relative transparency mapping of many types of lesions of the cornea and pachymetry with an almost instant display of the data to permit accurate assessment for the need of surgery.

One of the very important contributions of the present invention is the fact that it operates on a real time basis to provide almost immediate results. In this respect, the invention operates in real time in that it provides data to the operator of the instrument and can also provide a corneal mapping, essentially at the same time as the examination of the cornea is being made. Thus, and even though there are processing delays involved, these delays are trivial compared to optical resolution and processing of the user and therefore, the invention effectively operates on a real time basis.

The ophthalmic instrument of the invention preferably exists in the form of a densitometer or a pachymeter, as aforesaid. In this case, the invention comprises three major subsystems which are a modified slit lamp for projecting beams of light onto the eye to be examined, a television camera and associated lens system for obtaining the image of the eye to be examined and electronic circuitry for defining and quantifying a portion of the television image. A drive mechanism is provided for moving the optical slit to produce successive images for analysis. Associated computer software performs the requisite drive mechanism control, image selection, digital conversion of the analog television signal for computer processing and numerical analysis for converting the information into a viewable measurement of surface shape, thickness, optical density area and display of the derived information for clinical use. A video output of this type is effective for display, teaching and/or record keeping.

To the extent described herein, the ophthalmic instrument of the present invention is somewhat similar to that instrument and the method herein is similar to that method described in the aforementioned co-pending U.S. patent application. One of the important aspects of the present invention is the fact that the instrument of the present invention utilize a multiple Scheimpflug corrected slit projector in order to avoid the conventional image distortions which can otherwise arise. Thus, in accordance with the present invention, it is possible to fit a sequence of images accurately to form a reconstructive surface of the cornea.

The use of the optical slit Scheimpflug corrected projector of the present invention enables correction of slit translation of the path for correcting lens geometry, lens shape and anterior chamber depth. Thus, with the system of the invention, it is possible to correct for loss of depth of focus and which enables measurement of the depth of the anterior chamber of the eye and the shape of the crystalline and lens of the eye in a much more repeatable manner and more accurately.

The ophthalmic instrument comprises, in broad terms, a light projecting means, such as a projector, for illuminating a defined area of the cornea. An imaging means, such as a television camera, provides for a television image of selected portions of the illuminated area of the eye. A video means, such as a video amplifier, receives the image of the eye and generates and transmits a video signal representing the image of the eye.

The video signals, which are derived by the video means, operate in conjunction with a converter means for converting these video signals into a digital format. The converter means may adopt the form of an analog-to-digital converter which operates in conjunction with a computer having a data memory. A fiducial means delineates portions of the video image for focusing and alignment. A suitable computer program delineates these portions of the video signal to be converted into this digital format. Finally, an analysis means is provided for detecting and storing the relative brightness levels within the delineated areas in the aforesaid data memory. An address counter is also employed to enable subsequent addressing of the stored information.

The present invention also relates to several processes associated with the finding of thickness and relative optical density of the cornea of the eye, as well as ascertaining extent of lesions or other optical discontinuity. In one aspect, the invention comprises a method for ascertaining the extent of the lesion or other optical discontinuity of the tissue of the eye. This method utilizes the steps of illuminating the tissue area to be analyzed. An image is generated and this image is quantified. Portions of the image which contain the lesion are delineated and a reference area is also delineated. Thereafter, the delineated areas of the image are converted into digital form for subsequently analyzing the numerical magnitude of the digital form data.

In another aspect, the present invention provides for a method of ascertaining the surface shape and local thickness of the cornea of the eye. In this case, the method involves selectively illuminating the tissue area of the eye and quantifying the image of that tissue. Again, portions of the corneal image are delineated and a reference area is also delineated. These delineated areas are then converted into digital form for subsequent analyzing of the relative numerical magnitude of the digital form data.

The invention produces surface contour maps of the cornea of the eye and comprises projection illumination means for producing a definable spacial delineation of corneal contour. A television camera means renders the illuminated areas into electrical analog form signals. The analog signals are converted in a digitizing means for computer-legible operation. A computer means calculates the corneal surface shape from the digital signals.

This invention possesses many other advantages and has other objects and advantages which will become more clearly apparent from a consideration of the forms in which it may be embodied. The following detailed description and the accompanying drawings illustrate one of the practical embodiments of the invention, although it is to be understood that this detailed description and the accompanying drawings are set forth only for purposes of illustrating the general principles of the invention. Thus, it is to be understood that the detailed description and the drawings are not to be taken in a limiting sense.

OVERVIEW OF THE INVENTION

Densitometry is a term applied to measurement of the optical density of areas of photographs. Densitometers commonly measure the log of the reciprocal of the percentage of light transmission for a defined area at a stated wavelength or wave band. Measurement of the relative reflection of scattered light is commonly employed to define turbidity in water samples. The amount of light scattered and thus retro-reflected is compared to a known reference value in this process.

The densitometer of the present invention measures the relative magnitude of reflected light from scattering within ocular tissue as an indication of the optical density. In the strictest sense, this is not a true density measurement but the data derived are a measure of the relative transparency of the corneal tissues. The corneal interface with the air is not affected by stromal opacification and serves as a relative density reference for the measurement. The minimum reflectance value for calibration use is derived from the signal representing the anterior chamber over the pupil where the average reflectance is minimal. The optical density of small and large areas often provides diagnostic data for determining the need for surgical intervention. In addition, surface contour and the thickness of the cornea are quantified for producing a complete, three dimensional thickness map of the cornea including local thickness of the membrane.

The present invention uses light from a conventional light source, such as an incandescent lamp, in order to enable an analysis of thickness and optical density of the cornea at one or more wavelengths. Successive exposures are made with a small linear movement of the slit image between each exposure producing a series of density images which are then stored. These images are, in effect, Tyndall images and produced largely by Rayleigh scattering. For this purpose, broadband illumination is employed to obtain the Rayleigh scattering.

The Rayleigh scattering is the same effect which causes the sky to appear blue and is characterized by the relationship, $1/\lambda^4$ The displayed reconstruction of these slices is similar to that used for computed axial tomography and the like which is well known in the art. The motion of the slit which forms the object in the slit projection system is inclined to the axis of projection by an angle chosen to satisfy the Scheimpflug condition. The slit structure differs from classical design in that the slit is curved along the axis perpendicular to the optical axis to provide additional depth of focus at the cornea. A three dimensional display the anterior chamber depth and local corneal thickness is also provided to the user for planning anterior segment surgery as described for single sections by Lehrman et al. Measurement of anterior chamber diameter and biometry of anterior segment by Scheimpflug slit lamp photography, supra.

The slit lamp is a common instrument employed by optometrists and ophthalmologists for examination of the anterior portion of the eye. Many different versions of the instrument have been produced over the last century but all have three elements in common, which include (1) a projector for providing a collimated image of an optical slit focused on the eye, (2) a bio-microscope and/or camera for viewing the image formed by the projector and confocal with it, and, (3) a mechanical system for supporting the subject, the projector and the viewing system where the elements can be positioned relative to each other for examination of the eye.

The thickness plot produced by the present invention is accurate and repeatable for providing the surgeon with the data required for planing radial keratotomy or other refractive surgical processes. Localized opacities are also mapped by the present invention for planning corneal replacement surgery. Corneal wounds and ulcers are also mapped providing accurate diagnostic information to the physician. In general, changes in index of refraction associated with scaring or ulceration create foci of light scattering and loss of transparency. The index of refraction in the bulk of the cornea is less in the fluid than in the fiber cytoplasm and scattering results from the optical discontinuities. The cornea may be damaged by disease processes, mechanical forces or foreign object penetration. In these cases the opacification is probably due to the changes in protein molecule orientation at the injury site in healing. The degree of opacification can be monitored by loss of visual acuity but the loss of night vision due to loss of image contrast may be debilitating in some cases where the Snellen acuity is only slightly affected.

The ability of the present invention to quantify the degree of opacification and measure the locus of localized changes provides a tool for assessment of corneal disease and scarring which would require surgical intervention. In some instances, the localized changes in refractive index may be located away from the optical center of the cornea and does not interfere with vision to any great extent. In these cases there is a high probability of degeneration of visual acuity over time even though the traditional snellen test does not indicate any current loss of visual acuity. Localized opacifications may also produce monocular diplopia due, in part, to diffraction at the edges of the opacification which may be masked by the constricted pupil in conventional testing methods.

Testing of contrast acuity and low light level testing when such opacities exist tends to demonstrate the loss of night vision adequate for safe driving precedes the loss of snellen acuity. Slit lamp examination will reveal the presence of these abnormalities but direct visual examination does not provide accurate and repeatable assessment of the lesion location, density, area and any changes in size or opacity with time. The present invention provides a tool for repeatable assessment of potential vision loss under adverse lighting conditions. The present invention provides for mapping all types of corneal opacities, as well as corneal contour and thickness in a single instrument.

A beam of sunlight entering a darkened room through a hole in a curtain forms a visible path due to dust particles, water droplets and smoke in the air. The slit lamp uses the same principle for visualization of the scattering of light in nearly transparent tissues to render visible structures which can not otherwise be seen. Focal illumination is employed in the present invention by a modified conventional Köhler projector. The object at the focal plane is one or more optical slits which may be moved in the focal plane by an associated computer controlled mechanism or related drive mechanism.

Construction and movement of the slits into a curved surface which is moved according to the Scheimpflug rule provide substantial depth of focus enhancement over prior art systems for greater accuracy of measurement. The image of each slit is made confocal with a television camera which forms a part of the instrument of the present invention so that the instrument may examine various areas without repositioning. The focal length of the projection lens is as long as possible to reduce the convergence or divergence of the beam over small axial distances. The aperture sine of the projection system is preferably on the order of 0.05 to limit the defocusing effect with depth caused by projected beam convergence, and the focal ratio is calculated by well known technique for producing optimal brightness and sharpness of the illuminated area.

The projector and the camera are mounted on a common vertical member to allow the projected thin sheets of light to enter the eye at an angle to the camera axis and to permit horizontal, vertical and axial alignment with the eye. The beams of light produce diffuse reflections from each successive portion of the anterior part of the eye through which they pass. The proper selection of slit width and position produces the illusion of a cross section of the cornea as a luminous band against a dark pupil.

The "Tyndall phenomenon" is the term employed to describe the aforesaid method for generation of an optical section of the eye and which is well known in the ophthalmic art. The diffuse reflection from the first of the layers of the cornea which provide the optical section image is used in the present invention as a reference against which the diffuse reflection from the other portions of the cornea are compared for determining the relative transparency.

The present invention replaces the conventional biomicroscope of the common slit lamp with a television camera system for producing digital images for analysis of the anterior portion of the eye. The size of the image formed at the focal plane is determined by the focal length of the lens employed and the distances from the lens to the image and object planes. The distance of the image is to the size of the image as the distance of the object is to the size of the object. The common "opticians formula" relates the image and object distances to the lens focal length.

$$1 \div o + 1 \div i = 1 \div f$$

Here the object distance o, the image distance i, and the lens focal length f are related. The magnification factor, m is derived from the numerical ratio between i and o.

In a finite conjugate system such as the slit lamp system, the effect of minor changes of optical path length are significant. The inclination of the slit image to be examined to the optical axis of the projector causes the object distances to vary over the width of the eye. The change of distance also causes defocussing of the image of the slit in parts of the image space which degrades the image quality for analysis purposes. The slit mechanism is inclined relative to the optical axis of the projectors by an amount determined by the Scheimpflug rule to eliminate most of the defocusing caused by the path inclination. When the present invention is used for corneal analysis but not anterior depth information, the slit is also formed as a section of a cylinder as opposed to the planar form for still greater enhancement of the image for analysis. The eye, camera and projector relationships are derived from these elementary formulae.

The width of the slit may be increased to provide greater illumination to compensate for the exposure loss due to small aperture but resolution of the densitometric data will also be reduced by some amount. When photographs of objects close to the camera are made, the depth of focus is dependent upon the lens focal length and the iris opening. The sensitivity of the camera and the illumination system define the slit geometry and illumination constants.

In ophthalmic photography with a conventional slit lamp camera there is little choice over iris opening and none over focal length. The design of the instrument imposes severe light losses and provides at best about f16. The use of a single lens system in the present invention permits focal ratios of f2.8 which permits a considerable reduction in illumination levels and consequent reduction in the possibility of photo-toxicity. In the preferred embodiment, the magnification ratio is close to 1:1 which provides the desired image for analysis with good overall focus. The data provided by the present invention can be used to better plan cataract surgery and especially the computation of the power required for an intra-ocular lens implant.

The ocular instrument of the present invention measures the elemental brightness of a selected portion of a Tyndall image of the eye. Selection of a portion of the field of view of a slit lamp system is operator controlled through the use of fiducial marks delineating an area in the video display. The elemental amplitude within the delineated area is determined by subdividing the video image line segments selected into small picture elements or "pixels" which are examined and quantified for brightness information. There is a definable relationship between the pixel and the size of the image on the camera faceplate and hence the object.

The present invention provides a system for further reducing the number of loci used in the calculations by circumscribing a portion of the visible frame to encompass the area of interest and storing the resultant information in more compact form without loss of resolution or accuracy. Because the location of the Tyndall image within the video frame is predictable as is the maximum sagittal height of the curved image, the data in storage can be selected to define the location of the segment of interest. The limbus is also definable in location and size in the video image. The location of the limbus is defined by an area between two concentric circles with diameters of 11.5 and 13 mm object plane referred. Centered in the image is the reflection of the fixation lamp with associated Purkinje image reflections as well as the specular reflection of the two slit projectors. A small aperture in each slit assembly is positioned to provide a fixed Tyndall image spot from the projector not currently projecting a slit image. These spots are used for defining the Z axis motion of the eye in the set of sequential images which comprise the measurement. These optical and anatomical landmarks are used for fitting the sequence of images into a single coherent definition of the corneal topography.

The high inherent sensitivity of modern television cameras together with the ability to shape the gamma curve for calibration in the present invention provides a considerable improvement in raw data quality over the photographic process of the prior art. The width of the Tyndall image of the cornea is, in effect, a measure of corneal thickness. Thickness determination is based on a ray tracing principle. Since the entrance angle of the ray from the keratometer is known, the index of refraction defines the ray path in the cornea. An intersection of this ray path with a ray back traced from the camera provides an angle of incidence from which the thickness determination is a trivial solution.

Due to the fact that the brightness of the Tyndall image at the cornea differs from the almost constant anterior corneal surface reflex, a simple numerical amplitude discrimination process is used to define points within the circumscribed fiducial area. The numerical values for the pixels so defined are then used to define the optical density in terms of relative scattering of light by location within the cornea. The optical density is further corrected by compensating the measured brightness of each pixel for the losses due to the density of portions of the path through which the illuminating and scattered light travels and by conventional gamma correction circuitry. Histogram correction or other well known techniques may also be employed for enhancing the values defined for the Tyndall image in storage.

The shape of both anterior and posterior surfaces and hence thickness of the cornea of the human eye can be mapped by means of the Scheimpflug corrected slit projection system of this invention. The line of gaze fixation is made coincident with the optical axis of the camera by a target viewed by the subject via a beam splitter or inclusion in the camera lens system. The beam splitter or other fixation target is so positioned as to cause the desired alignment of the eye and camera, and thus, the slit beam. The coaxial location of the fixation target insures that the visual axis of the eye being examined is coincident with the optical axis of the television camera. Beams of light formed by projection of an optical slit or slits are focused slightly behind the corneal surface. The beams are projected from known points located on a line at a fixed angle, preferably 45 degrees, from the optical axis of a camera and in the same plane.

At normal incidence, the reflection of light at a boundary between media of differing index of refraction is calculated as follows:

$$R=(n_2-n_1)^2/(n_2+n_1)^2$$

Where R is the reflected percentage of the incident beam, and, $n_1$ and $n_2$ are the indexes of refraction of the two media respectively. Thus, the air to cornea and cornea to aqueous interfaces will reflect a definable portion of the slit beam diffusely. The stroma or interior structure of the cornea comprises large muco-saccharide molecules in lamellar arrangement surrounded by saline solution. A similar diffuse reflection of a portion of the incident beam by Rayleigh scattering gives rise to the so called "Tyndall" phenomenon. The Tyndall image is the result of diffuse reflection at the optical discontinuities in the slit beam path.

Because the locus of origin of the slit beam relative to the optical axis of the camera is known, the shape of the Tyndall image, as viewed, describes the shape of the cornea. Taking a datum point on the Tyndall image, there is a displacement from where the slit beam would have intersected the reference plane, which corresponds to a function of the height of the surface at this datum point. After generating the anterior surface of the cornea, the posterior surface can be defined using the refractive index of the cornea and the angle of incidence for each ray derived from the anterior surface data by application of Snell's law. The beam is refracted into the denser medium by an amount calculated from the relative slope at each calculated ray entrance. The light from one or more slit projectors is also reflected by the corneal/air interface in specular manner. This reflex provides a check of the contour generated from the Tyndall data. The local slope of the cornea can be taken to be equivalent to a sphere of some radius when the surface area is very small. The resulting spherical mirror formed will act to reflect the incoming ray from the projector. The location of beam source and relative angle provides the basis for calculation. The image of the reflection is located in XY terms relative to the digitized image and the slope at the surface is calculated by the methods used by Placido which are well known in the art. The independent method slope derivation at points on both sides of the cornea, generally midway between the center and the limbus, provides quality assurance for the Tyndall image derived surface shape.

The cornea comprises a meniscus lens with positive focusing power. Gullstrand provides the most common "normal" focusing power of the cornea as 42.73 but it should be noted that the standard values given by Gullstrand for refractive indexes and radius of curvature calculate to 42.95. The surface shape is not constant due to the pulsatile pressure within the globe of the eye. This blood pressure induced change can be as large as a half diopter and there is no compensation in the prior art systems. The central 3 mm zone is taken to be spherical by Gullstrand and others in the schematic eye data for ease of discussion. The anterior surface has an assumed average radius of curvature of 7.7 mm. The posterior surface has an average radius of curvature of 6.8 mm. The thickness is on the order of 0.7 mm at the center and the effective index of refraction is taken to be 1.376. the anterior surface interface is with air and the posterior surface is with the fluid filled anterior chamber of the eye. The index of refraction of the fluid is 1.336. The usual formula $d=(n-n')/r$ yields the focusing power in diopters.

The following simple example will illustrate determination of corneal surface shape and thickness. Here, the radius of curvature r is expressed in meters and the successive indexes of refraction of the optical path yield the focusing power in diopters. The initial surface encountered by an entering ray is the tear film which has an index of refraction of 1.333 and is of almost constant thickness. Solving for the Tear film yields 43.25 diopters, the 5.58 diopter value for the anterior surface and for the posterior—5.88 diopters. The convex surface produces a negative lens on the posterior surface because of the reversed to normal order of refractive indexes. The total power for the standard "normal" cornea is then, 43.25+5.58−5.88=42.95 diopters. The range of possible surface shapes and thicknesses is quite large and the example given is for illustration of the relative magnitudes encountered.

Calculation of the surface shape in the present invention is by means of analysis of similar triangles. The anterior surface contour is defined first. The method involves simple geometric analysis of the Tyndall image. The angle between the slit beam and the optical axis is fixed at 45 degrees at center. The distance between the mirror and the eye is fixed at a known distance. The image point for each pixel is displaced from the optical axis as a direct function of point height above the reference base plane.

In the preferred embodiment of the present invention, the image to be analyzed is produced by projection of narrow bands of light into the eye by optical projectors of conventional "Köhler" design with Scheimpflug correction for focal depth. In the conventional slit lamp, the bio-microscope and slit projector are mounted on pivoted arms with a common bearing center so that the microscope and projector may be independently rotated in the horizontal plane while remaining confocal. In the present invention this arrangement of elements is preferably replaced by two slit beams from opposing sides with a constant angular relationship to the eye and camera. The image of segmented Tyndall illuminated areas of the half slits is formed in the plane of focus of the camera. The slit beams are angled to produce edge convergence of the Tyndall images when the axial distance between the central point of the cornea is at the desired distance and the camera and slit projector focal plane lies behind this plane at or near the iris. This construction provides the requisite known distance for all calculations and provides a simple operator clue to proper centering and focus.

The projectors of the present invention are preferably fitted with internal filters for determining the spectral content of the beam of light projected into the eye. The use of selectable filters to limit the spectral distribution of the illuminating beam provides the ability to quantify discoloration of portions of the cornea associated with age, scars or disease processes while limiting any potential phototoxicity from the light energy within the globe. The projectors used with the present invention are additionally provided with a mechanism for providing slit motion.

In the preferred embodiment, the slit assembly is moved under computer control in a direction at the Scheimpflug angle to the long axis of the slit when sequential image slice data are acquired. The slits are initially nearly centered and projected from both sides simultaneously. The position is calculated for the steepest cornea expected to provide adequate depth of focus for the optical systems. The resultant dual Tyndall image is used for determining instrument position to assure accurate focus and known magnification.

The operator positions the instrument so that the center of the two arcuate images are coincident and centered in the pupil. In an alternative embodiment, the slits used for focus and alignment are half length so that the ends are made coincident by instrument position forming an S shaped figure at the corneal apex. The construction of the instrument then provides the proper focus for the image series which comprises the pachymetric measurement.

The signal from the television camera is used to derive the relative image brightness of the corneal optical sections while the optical figure is being digitized and also viewed on the television monitor. Monitors for viewing both pictorial and computer signals are well known in the art and are not described herein.

Repositioning the slit beam by incremental motion of the slit perpendicular to the slit axis permits measurement of almost all of the cornea in detail and the composite time domain image data sequence is stored for analysis and display. The slit motion is interlocked in time with the vertical interval of the camera so that the successive images are stored over a very short time interval. In this way, loss of fixation or micro saccadic motion of the eye do not degrade the derived data. The action of a video analog to digital converter, called a frame grabber, serves to quantify the instantaneous brightness related voltage amplitude of each image element and to cause the sequence to be stored in a memory for later use. Subdivision of the video line into small spatial elements or pixels is by time interval selection in the frame grabber system.

The present invention makes use of common commercial camera and monitor apparatus without modification. Because the cornea of the eye is essentially circular in form, the normal television picture aspect ratio of 4:3, or the 5:4 ratio employed by many computer displays provides no advantage. In operation, the use of computer displays for television pictures deletes some of the picture in the horizontal axis. This "cropping" is of no consequence in the present invention. The most common camera tube is two-thirds inch (approx. 18 millimeters) in diameter. The desired image is on the order of twelve millimeters ore more in height. This assumes the limbus diameter is equal to the height of the image. The focal length of the lens and the size and location of the fiducial mark generation are determined on the basis of a square area which nearly fills the frame with the image in the vertical direction. The inner edge of the iris opening is also visible in the captured images and because the light does not always enter the pupil, the iris changes size in the course of the measurement. The shape and rate of iris motion are often of clinical interest and are available through appropriate computer programming.

For highest accuracy, each instrument must be calibrated after assembly to compensate for minor differences in system magnification and linearity to obtain maximum accuracy of the derived data. For this reason calibration means are provided as a part of the computer software and the user may check the calibration and reset the table values at any time.

One of the display functions commonly available from computers is the so called graphic format whereby lines may be positioned on the display screen under software control. The present invention makes use of this ability to define a portion of the image from a camera synchronized to the computer display which contains the image of the cornea to be defined. The computer controlled slit movement signal is coordinated with the pattern generation used to establish this cursor or fiducial mark system to define the portion of the image for computer analysis. Computer masking of the raw data is employed to reduce the calculation time. This technique reduces the number of data points to compute, increases speed and reduces artefact signal induced error in the analysis. The limbus is visible at least in a major part in each frame of data and the limbus image data are filed for each frame for sequential image fitting into the final surface determination.

A table is constructed in the microcomputer to provide a lookup technique of conversion for a range of measured brightness representing a range of known optical density values to any required degree of precision to assure accurate output data for the intended application. The lookup table is preferably constructed in a histogram analysis step where anterior surface reflectance is measured and the relative values obtained stored. Extrapolation between table entries is quite practical and reduces the number of table entries needed to assure accurate measurements.

The micro computer has provisions for graphic displays of bit mapped information in terms of X, Y coordinates on one of several pages of display memory. These data may take the form of pictorial and/or text type images in storage. Whole pages or portions of pages may be called for display on a frame by frame basis. The magnification to be used for the camera of the present invention is fixed and for this reason the area encompassed by the optical section and the constituent pixels are definable in terms of X, Y coordinates for all elements of the defined areas. The initial data sample is masked by selection of only that section of the image data which defines the corneal image. Each of the subsequent data samples which represent corneal sections is defined by a second range of loci which encompasses only the area of the Tyndall image. The pixel clock from the computer display system defines each pixel in storage and in the display.

Computer generated alignment points are displayed together with the picture of the eye. These fiducial points are placed over the corneal image by movement of the instrument by the user. The operator moves the instrument until the corneal image lies within the defined area, focuses the camera by axial motion until the desired focus figure is centered on the limbus within the frame, and then operates a switch to accept the data sample and to initiate the data collection sequence.

The light reflected from an optical discontinuity such as the corneal surface can be calculated by:

$$r = ((n_1 - n_2)^2 / (n_1 + n_2)^2)$$

Where the values of index of refraction, n, are 1.000 for air, 1.333 for the tear film and approximately 1.376 for the cornea and 1.336 for the anterior chamber fluid. From this it is clear that only a small fraction of the incident light will be reflected by the normal cornea. Any losses are calculated in the computer program to normalize the corneal image data for determination of the effective optical density of image points in the optical section.

In the prior art, the radius of curvature of the cornea is measured in the typical clinical practice by an ophthalmometer or keratometer. The image of an object of known size is observed as a reflection from the corneal surface. This convex mirror provides the data required for the calculations. In practice, the value of the sagittal height is small relative to the axial distance and is ignored. There are several fallacies in the calculation of corneal curvature even before the curvature is transformed into dioptric terms for use by the physician. The inherent assumption is that the surface is spherical and that in constructing a corneal surface map the central point is accurately defined. In fact neither of these conditions obtain in the clinical setting. The central point can not be derived because the instrument has a camera lens centered in the object which is a series of concentric circles illuminated from behind and because the reflection angle nears zero with fixed resolution in the frame grabber which causes the error band to rise asymptotically within the central two millimeter zone.

The surface contour map is constructed as a set of equivalent radius points from which slopes are defined relative to the central point which is not measured. This requires that the central surface be assumed to be perfectly spherical which is rarely the case. In addition, the lensmakers formula used as the basis for the computation is only true for paraxial rays from objects at an infinite distance and the error increases as the marginal rays are considered for surfaces removed from the center of the corneal mirror. The results are commonly expressed in dioptric form which introduces an additional error in that the corneal thickness and rear surface are unknown. The conversion of approximated surface shapes to focusing power in dioptric form uses a constant to adjust the value for better representation of the true focusing power but the fact that several manufacturers of keratometers and ophthalmometers use differing constants and, in some cases, tables of correction which are quite non linear demonstrates the inefficacy of the method. To express the focusing power of the cornea in dioptric terms the area so described must be a spherical surface and the corneal thickness and posterior curvature must be known. Even when the true corneal geometry is known, the non spherical surface over the area of the entrance pupil of the eye means that any dioptric representation is probably only an approximation and can not serve as a predictor of focusing power.

The present invention overcomes essentially all of these problems in the prior art determinations. The invention is particularly effective when using the Scheimpflug corrected slit projector and particularly, multiple Scheimpflug slit projectors.

BRIEF DESCRIPTION OF THE DRAWINGS

Figure 1:
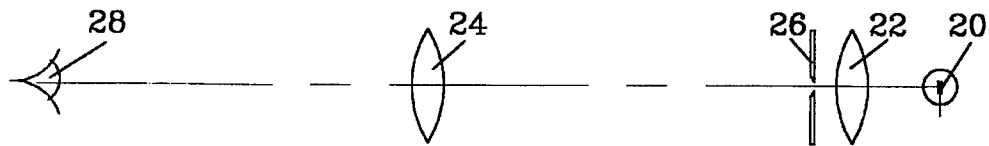
Figure 10:
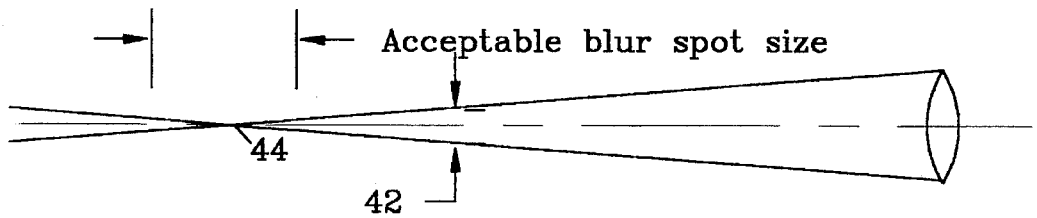
Figure 11:
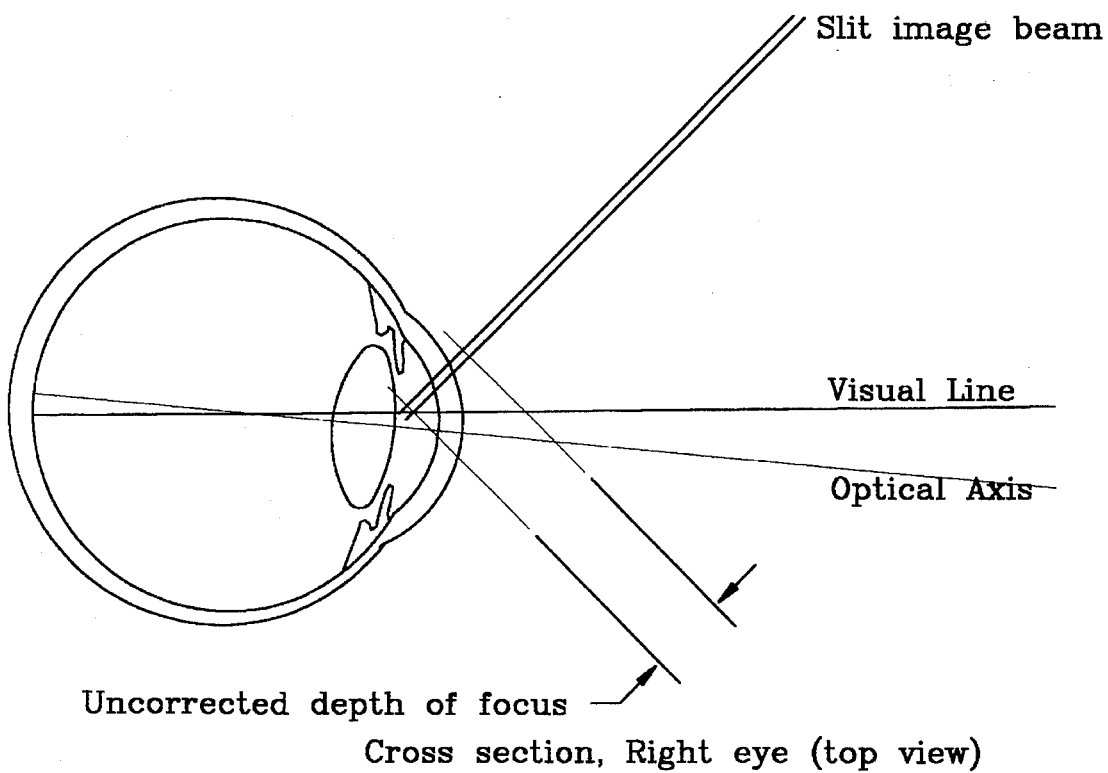
Figure 2:
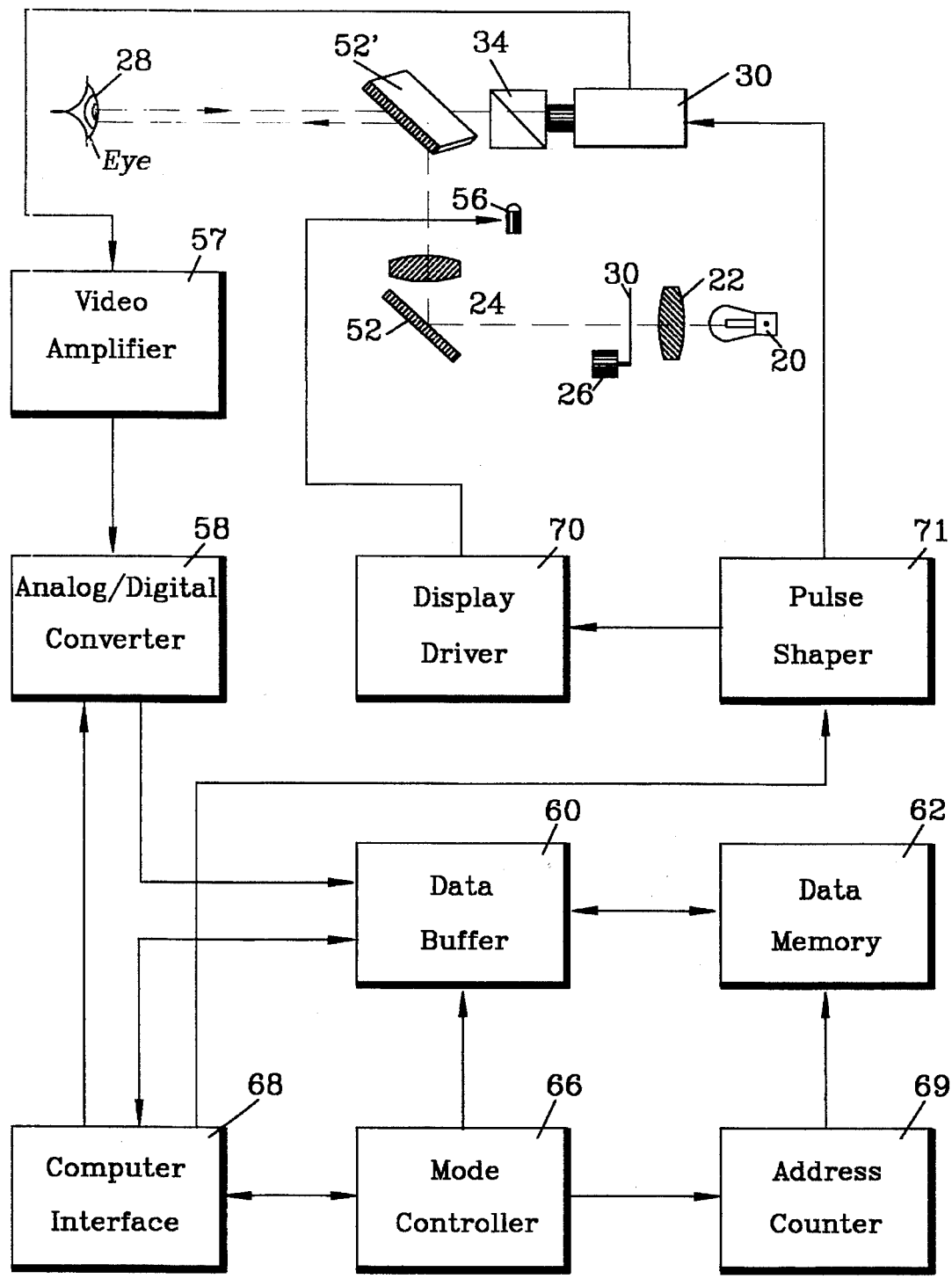
Figure 18:
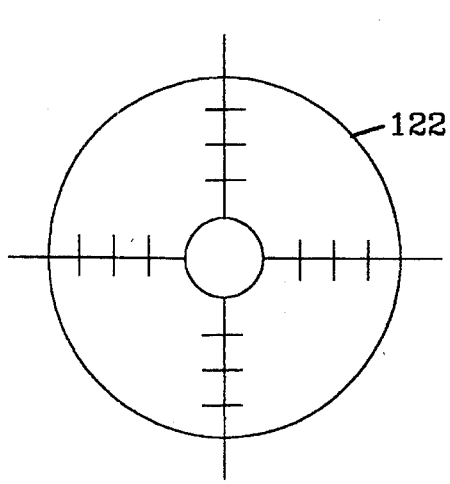
Figure 20:
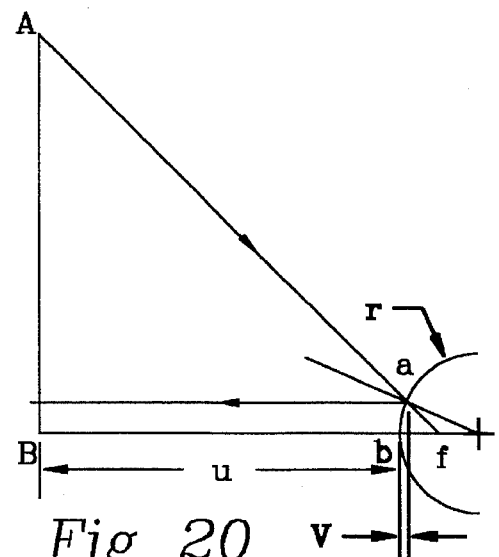
Figure 8:
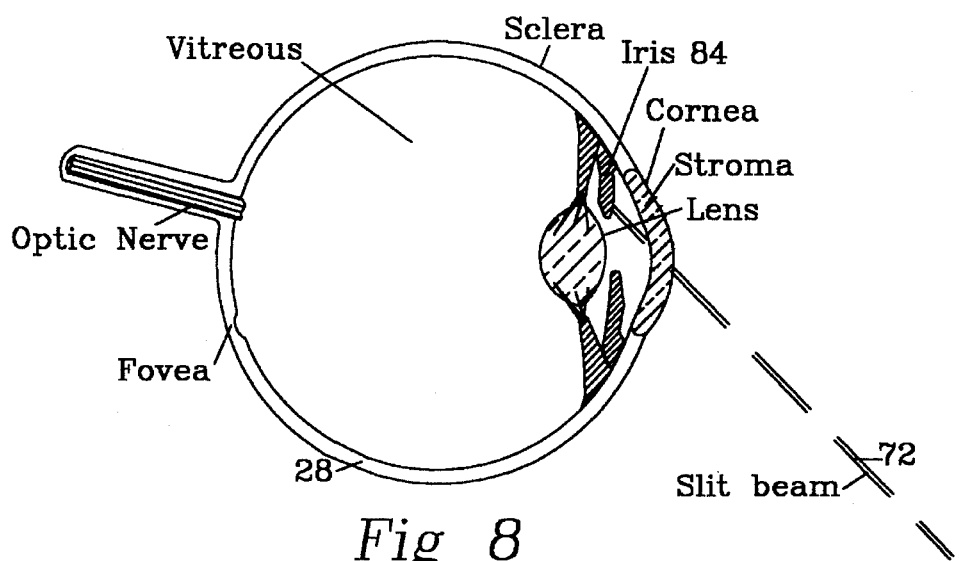
Figure 7:
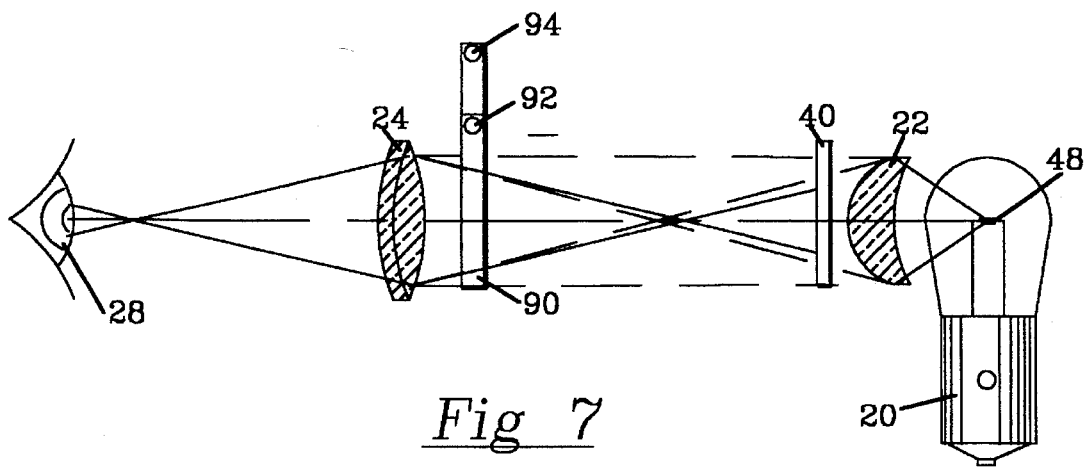
Figure 12:
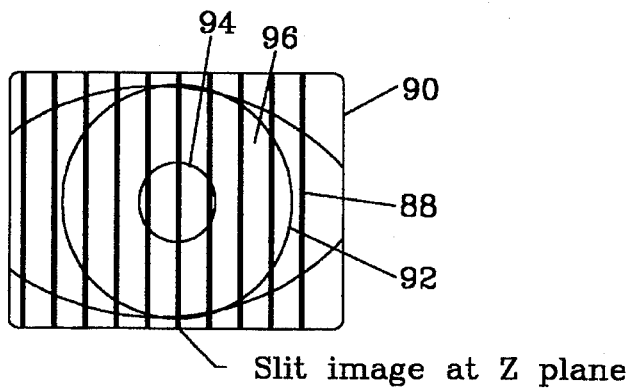
Figure 15:
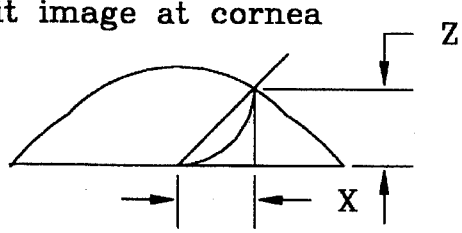
Figure 16:
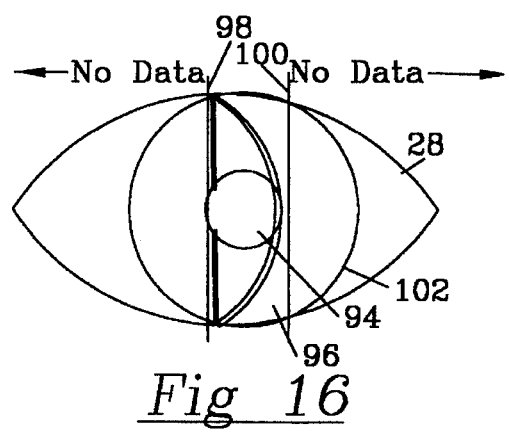
Figure 14:
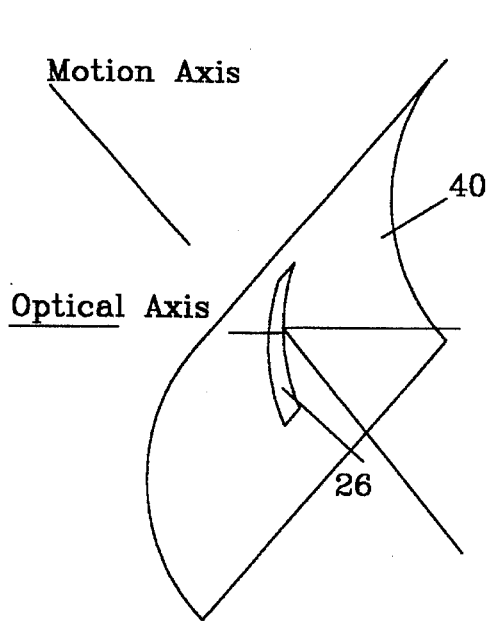
Figure 13:
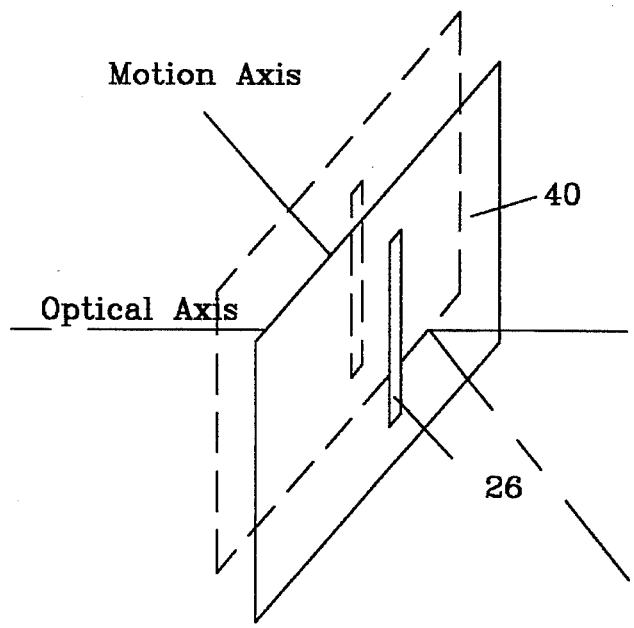
Figure 19:
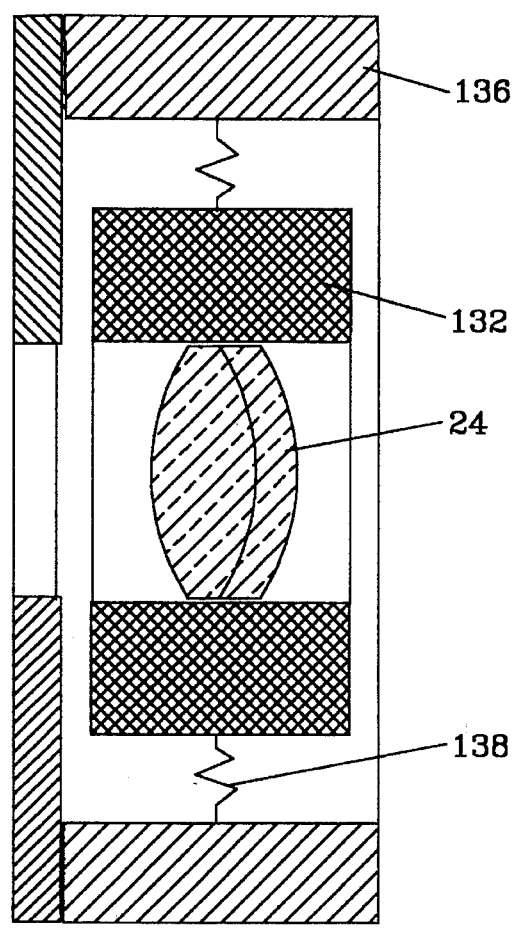
Figure 17:
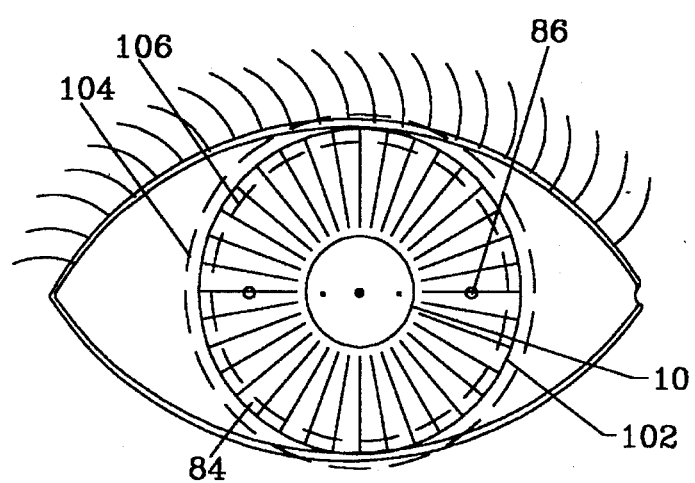
Figure 22:
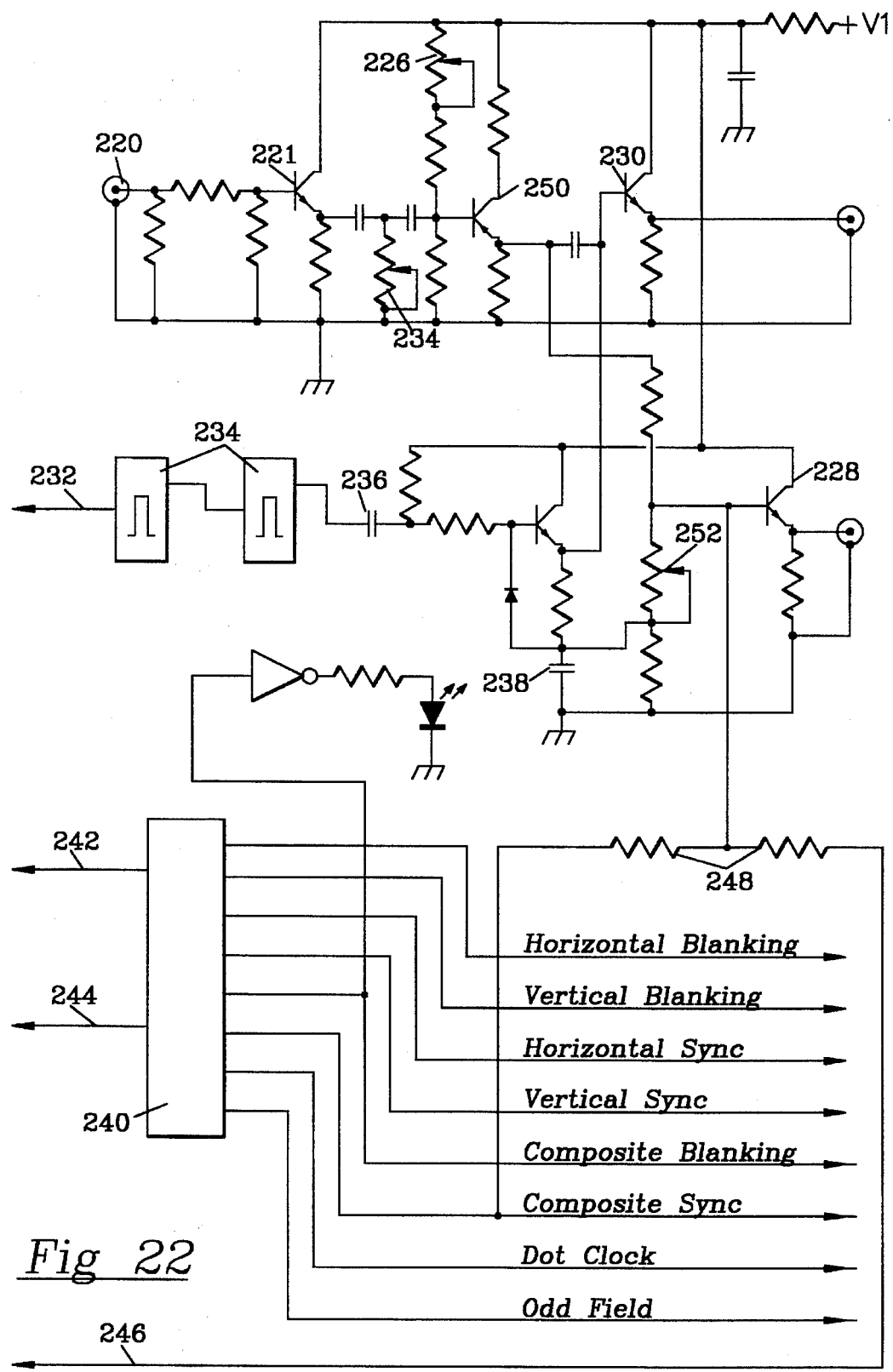

Having thus described the invention in general terms, reference will now be made to the accompanying drawings (nine sheets) in which:

FIG. 1 is a schematic view showing a beam of light from a slit lamp projector incident on an eye;

FIG. 2 is a schematic view showing some of the major components of the system of the present invention;

FIG. 3 is a top plan view, partially in horizontal section, of the optical instrument constructed in accordance with and embodying the present invention;

FIG. 4 is a perspective view of a focus aid mechanism forming part of the system of the present invention;

FIG. 5 is a front elevational view of the ophthalmic instrument of the present invention;

FIG. 6 is a side elevational view of the ophthalmic instrument of the present invention, partially in section, and illustrating the major components in the interior thereof;

FIG. 7 is a schematic view showing the optics and optical paths involved in producing a slit image at the eye of a subject;

FIG. 8 is an illustration of a horizontal cross section of the eye for reference purposes showing impingement of a slit beam thereon;

FIG. 9A illustrates a front elevational view of the eye with half-Tyndall images for focus and alignment superimposed;

FIG. 9B illustrates a front elevational view of the eye, similar to FIG. 9A, with the half-Tyndall images aligned and in the position where they would be centered in a fiducial mark;

FIG. 10 is a schematic view showing the effects of a beam convergence;

FIG. 11 is another cross-sectional view of an eye showing corrected and uncorrected depth of focus;

FIG. 12 is a front elevational view of an eye showing slit positions with respect to the eye and a slit image at a Z-plane;

FIG. 13 is a schematic perspective view showing the optical axis and a motion axis with respect to a flat slit;

FIG. 14 is a schematic perspective view, similar to FIG. 13, and showing a Scheimpflug corrected slit and the optical axis and motion axis relative thereto;

FIG. 15 is a graphic illustration showing a waveform representative of the slit image at the cornea of an eye;

FIG. 16 is a front elevational view of an eye showing horizontal reference planes thereon;

FIG. 17 is a front elevational view of an eye showing identification of areas which are examined by the instrument of the present invention and the providing of a measurement of a Z-axis motion;

FIG. 18 is a schematic view showing the fiducial figure employed for alignment in the present invention;

FIG. 19 is a schematic view showing the use of a voice coil system for providing fine adjustment of a depth of focus with the apparatus of the present invention;

FIG. 20 is a graphical illustration showing the geometry of the image analysis employed in the Placido method and in the present invention;

FIG. 21 is a graphical illustration showing a television wave form which may be produced in the system of the present invention; and FIG. 22 is a schematic diagram of a portion of the electric circuitry employed in the system of the present invention.

DETAILED DESCRIPTION OF PREFERRED EMBODIMENTS

System Overview

Analysis of the Tyndall image of an optical slit for construction of a topographic map of the cornea and lens of the eye has suffered from inadequate depth of focus in the associated optical systems which has reduced the accuracy of the resulting diagnostic data. The present invention addresses this problem to enhance the quality and efficacy in clinical ophthalmology. Scheimpflug correction of the depth of focus of the camera has been used in some instruments but with limited success because of mechanical constraints. The prior art involves Scheimpflug correction of the camera optical system which is not practical when using a dual projection system as in the present invention.

The instrument of the present invention provides adequate depth of focus for the projectors by application of the Scheimpflug principle to the slit projection systems and addresses the camera depth of focus required for measurement of both the lens and cornea which is not possible with existing systems. The camera lens is moved between sequential measurements by a voice coil system under computer control. The area of the video image which contains the portion of the image to be studied is selected by the computer program to reduce the amount of data which must be analyzed and hence the time required for the test.

A fixation target is viewed by the subject as a cross on an illuminated background to assure that the point of gaze is coincident with the optical axis of the camera. The target is imaged with a single lens and viewed through a beam splitter in front of the camera lens to place the target in the desired relationship. Reflection of the target and the exit pupil of the projectors by the tear film on the cornea are used together with spot projection and limbus location for alignment and registration of the sequence of exposures which comprises a complete measurement.

Optical Systems

Referring now to FIG. 1, two slit projector systems are employed. Each of these identical projectors is directed at a common point and focussed at a point slightly more proximate to the projection lens. The system includes an illuminating light source lamp 20, preferably of the Halogen cycle type. The lamp 20 provides broad spectrum illumination which is focussed by a condenser lens 22 at the entrance pupil of a projector lens 24. An optical slit 26 is mounted at the object plane of the projection lens 24. Light from the lamp 20 via the condenser lens 22 and the action of the projection lens 24 produces an image of the slit 26 at the eye 28. The focussed image of the slit 26 generates a Tyndall image in the cornea and lens primarily by Rayleigh scattering.

This virtual cross-section of the anterior portion of the eye is analyzed for mapping of the structure of the eye. A three-dimensional mapping provides diagnostic information to the user which is an aid in planning ophthalmic treatment. The projection lens 24 is mounted at some distance from the eye and in consequence the illuminating beam converges.

System Components

The main overall components which form part of the system in the optical instrument of the present invention are more fully illustrated in FIGS. 2–6 of the drawings. The instrument of the present invention comprises a television camera 30 having a conventional lens and which is aligned with and receives an image of the eye 28 of a subject through a beam splitter 34 for later quantification and for providing a television image of the eye for analysis. Referring to FIG. 4, it can be seen that the apparatus comprises a conventional incremental motor 36 for positioning an elongate aperture which constitutes the slit 26 in the focal plane of a light projector represented in FIG. 1 by the lamp 20. The slit 26 is contained in a slit form 40. The slit form 40 may be operatively connected to a suitable slide assembly 42, as also best illustrated in FIG. 4 of the drawings.

The slit form 40, and particularly the slit 26 thereof, in conjunction with the lamp 20, will produce an image at the eye 28 through the action of the projection lens 24 as shown in FIGS. 1 and 10 for selecting sequential images for analysis. FIG. 10 illustrates the effect of beam convergence of the illuminating beam. The convergence angle 42 causes the beam to be wider at axial distances remote from the focal plane 44. The circle of confusion is dependent upon the focal distance and the exit pupil diameter.

The sine of the half angle of convergence has been established at 0.05 for conventional slit lamp in slit lamp photography. For best accuracy, the present invention uses a distance and aperture size which produces an aperture sine of less than 0.01. The reduced level of illumination is compensated by an increase in light from the lamp 20 and the use of a sensitive camera system. The total energy at the corneal surface is not increased since the use of a smaller aperture is offset by increased lamp energy so that subject safety is not compromised.

Referring now to FIG. 7, there is illustrated a Köhler arrangement which comprises the lamp 20 having a dense filament 48. In this case, by further reference to FIG. 7, it can be seen that the image of the filament 48 is formed at the entrance pupil of the projection lens 24 by means of the condenser lens 22.

Adjacent to the condenser lens and in optical alignment with the condenser lens 22 is the slit form 40 carrying the optical slit 28. This slit form 40 is preferably mounted on a carrier (not shown in detail). The carrier is moveable in a direction perpendicular to the slit 26 by the aforesaid incremental motor 36. The images of the slits are brought into focus in the same plane as the television camera 30 by the projection lens 24 and a system of mirrors and prisms, including a regular mirror 52 and a dichroic mirror 52' (both of which are interchangeable), as shown in FIGS. 2, 3, 5 and 6.

A fixation lamp 56, sometimes referred to as a "target lamp" or "fixation target lamp", as shown in FIG. 2, is also provided for operation with the beam splitter 34, as shown. This combination of the lamp 20, lenses 24 and 22 and mirrors and prisms 54, as well as the slit form 40, function as a slit lamp projector.

Referring again to FIG. 2, it can be seen that the television camera 30 generates a signal representative of the image of the eye which is transmitted to a video amplifier 57 for amplification and mixing video signals for analysis. A flash analog-to-digital converter 58 receives the output of the video amplifier 56 for processing and digitizing analog signals received from the television camera 30. A data buffer 60 receives an output from the analog-to-digital converter 58 for directing the digital data to and from a storage in the form of a digital data memory 62. For example, the data buffer 60 and the data memory 62 may form part of a conventional computer which is not illustrated in detail herein. In this respect, it can be observed that many of the components are shown in schematic form (rectangular boxes) in FIG. 2.

The digital data which is directed to the digital data memory 62 constitutes a storage of the numerical brightness of each element within the fiducial boundary. An address counter 64 is provided for determining the location and storage of the pixel brightness data for each pixel in the image. A mode controller 66 is connected to the address counter 64 and is provided for determining the sequence of operations of the system. The mode controller 66 receives an input from a computer interface 68 which, in turn is connected to the data buffer 60 and is also connected to the analog-to-digital converter 68, as illustrated in FIG. 2.

The computer interface 68, operating in conjunction with a computer, controls the system elements through the associated computer. In this case, a display driver 70 is provided for controlling the aforesaid fixation target lamp 56 visible by reflection by the beam splitter 24. This serves to render the apparent location of the fixation target lamp 34, namely from the beam splitter 34, coincident with the optical center of the television camera 30 and its associated lens system. A pulse shaper 71 is connected to the computer interface 68 for controlling the operation of the television camera 30.

Turning now to FIG. 8, it can be observed that there is a representative image of the eye 28. The slit beam 72 illuminated anatomical features are visible Tyndall images.

Referring to FIGS. 9A and 9B, these images are visible as a Tyndall image 82 representing those portions of the eye, such as the corneal epithelium, the stroma and the endothelial layer which scatter the light. An iris 84 in the eye is not the area to be measured and therefore, the illumination of this area is an artefact of Tyndall illumination. The iris image 84 may further be diminished by limiting the spectral distribution of the slit beam 72 through the use of a color filter (not shown). In addition, a slit projector, or slit projectors if more than one is used, produce specular reflections 66, as shown in FIG. 9A, and which are located in "X, Y" coordinate space, depending upon the surface curvature of the cornea of the eye 28. The associated computer, through the action of the computer interface 56 and the mode controller 66 and display driver 70 (see FIG. 2), restrict the sample data to the corneal section of the eye made visible by slit illumination. The iris 84 may be dilated maximally to provide a uniform dark background for the optical section and the slit height, which is restricted to eliminate bright reflections above and below the area of interest.

Slit Image Analysis

Referring now to FIGS. 11, 12 and 13, the optical slit 26 mounted in the slit form or so-called "carriage" 40 is moved in a translational fashion in the object plane of the projection lens 24 in a direction perpendicular to the long axis of the slit 26. The direction of motion is at an angle to the optical axis of projection selected by the Scheimpflug rule to increase the depth of focus of the projected image at the eye 28. The motion of the slit 26 and associated carrier 40 is in steps which are in time synchronism with the television camera 30 so that a sequence of static slit images 88 (FIGS. 12) are formed in the sequence of television images 90. The image of the limbus 92, the pupil 94 the Tyndall images 82 (FIG. 9B) and the iris 96 (FIG. 12) are recorded by digital conversion of each of the several frames which coincide with the incremental motion of the slit 26.

While one slit 26 is being so moved, a second slit and associated carrier of a second projector is so positioned as to place the image of a small aperture at a known location on the eye. This Tyndall image is used to provide Z axis data for the subsequent fitting of the data from the several discrete images from each side into a single coherent surface reconstruction in cartesian terms. The sequence of Tyndall images is examined for location together with certain landmarks and combined by the computer program into a complete surface map with any eye motion compensated by the landmarks to assure spatial registration of the entire data sequence.

In the preferred embodiment, as illustrated in FIG. 14, a modified slit carrier 40' may be formed as a section of a cylindrical surface as contrasted to the preferred planar form. The slit carrier has a curved slit 26'. This causes the plane of focus of the slit image to more closely conform to the surface shape of the cornea and lens of the eye and reduces beam convergence errors which must be compensated for but it is only effective for analysis of the corneal surface and induces an additional error term for the analysis of lens shape. Where the lens is not mapped, the cylindrical form of the carrier 40' can provide some improvement in the raw data of corneal surface topography.

Referring now to FIGS. 15 and 16, the discrete location of the slit 26 for each of the sequential exposures produces the well known Tyndall image of a cross-section of the cornea and lens of the eye. Because the beam projection angles for each discrete slit position are known, the sagittal depth of any element of the anterior structure of the eye may be derived from the X,Y coordinates derived from the television image sequence. The nature of the image relative to the instantaneous slit position is known so the data formed by digital conversion of the image may be examined in small sections. The Tyndall image must lie in an area bounded by the limbus, the location of the undeflected slit at the Z reference plane and a point defined in X, Y terms by the sagittal depth of the steepest corneal surface anatomically possible. The ends of the Tyndall image are always at the brightly illuminated portion of the iris where the slit beam strikes for further simplification of the problem of locating and tracing the edges of the Tyndall image.

The location of the area of the image which must contain the Tyndall image is defined for each possible slit position by a set of numerical constants for the horizontal loci 98 and 100 (FIG. 16) which are established by mechanical construction and stored in the computer program. This technique greatly reduces the number of mathematical calculations required for analysis of the images and subsequent construction of a topographical map of the eye 28. The number and location of the slit images defining a measuring sequence is variable under program control for fine analysis of small areas by small slit motion increments, increased number of slit positions for anesthetized or mechanically fixed eyes, etc. This flexibility of data collection increases the utility of the system over prior art systems which have fixed resolution and area of coverage.

Referring now to FIGS. 16 and 17, the data to be analyzed for three dimensional mapping of the anterior of the eye 28 are made over a short period of time which is typically less than one second. Because the cornea is a flexible membrane supported by the pressure of the fluid within the eye, the surface is deflected slightly by the pressure changes induced by the cardiac cycle. In the conventional keratometer, the single image is at an unknown part of the cardiac cycle which induces an error and poor repeatability between measurements. Additionally, tension on the zonules from the muscle tissue (ciliary tissue) within the globe to change plane of focus, produces attendant changes in the shape of the globe which are compensated for by fixation at optical infinity so that the subject is not accommodating.

The present invention compensates for pressure induced variations in surface contour as well as micro-saccadic motion of the eye in the course of the sequence of image collection. The inclusion of sufficient time in data acquisition for an entire cardiac cycle is, in part, the key to this correction of surface topography. The compensation is performed by the analysis of surface reflections and a system of landmarks. The limbus 102 is a constant which is used in the sequence fitting. Because any motion of the eye will shift the apparent location of the limbus 102 in the sequence of images, the detection of this physiological landmark is employed for registration of the image sequence. The location of the limbus 102 within the individual frame in the sequence is definable.

A pair of concentric circles 104 and 106 are mathematically defined in the computer program. The image of the limbus should always fall within the defined space between the circles 104 and 106. This simplifies identification and measurement of limbus location. If the limbal image falls within the defined space the sequence can be fitted into a single coherent map data structure. The area defined by the circles 104 and 106 comprises the only area which must be examined by the edge detection program and which reduces the complexity of data analysis. Areas are defined from an exposure prior to slit image placement on the cornea which has the Tyndall image of two small spots, one from each projector. The slit motion of one projector at a time leaves one of these spots visible in every data image in the sequence. The relative location of the centroid of this image is effective in providing a measure of Z axis motion of the eye similar to the X, Y axis data from the limbus (supra). The exit pupil of the projector lenses and the fixation target produces a set of purkinje images which also serve to provide surface location data for deleting motion error from the topographic data set. The time required for the measurement is significant in clinical practice and must be as short as possible for the instrument to be a useful tool for data collection.

The operator of the ophthalmic pachymeter is provided with a computer-generated figure which is used as a fiducial mark system illustrated by reference number 110 in FIG. 18. The fiducial marks in this fiducial mark system are located around the center of the display monitor. The figure is preferably software-controlled to coincide with the measured locus of the system center and which is the intersection of the optical axis with the zero reference plane, as shown in FIG. 11. This is accomplished by operation of the incremental or "stepper" motor 36 which moves the slit form 40 and hence, a half slit 92 also in this form 40. (See FIG. 3) Thus, the computer generated fiducial marks are designed to be coincident with the true image center, regardless of camera tolerance so that the operator is provided with an alignment aid. Thus, the computer generated fiducial marks are designed to be coincident with the slit position so that the operator is provided with a focus and alignment aid.

Referring now to FIGS. 5 and 6, it can be seen that the slit lamp illuminator components, e.g. the lamp 20 and slit form 40, as well as the television camera system 30 are mounted on a moveable base 114 which comprises a frame casting. A vertical positioning element, in the nature of a vertically arranged support shaft 116 is operative mounted on the base casting 94, as illustrated. Generally axles 118 which support toothed wheels (not shown) are located in the base casting 114, as best shown in FIG. 5 and 6, for motion toward and away from the subject. A main housing 120 is mounted at the upper end of the support shaft 116 and contains the major components forming part of the apparatus, as for example, the light source 20, the television camera 30 and those other components as best illustrated in FIGS. 5 and 6 of the drawings. The device also comprises dust covers 110 which cover the toothed wheels.

A friction creating member 122 is operated by a lever or handle 114 against a table surface 117 to cause the instrument to be moved by the operator for focusing and alignment. This arrangement allows for motion toward and away from the subject, as indicated. The base casting 104 is provided with internal bearings (not shown) to permit the assembly to move transversely, that is perpendicular to the forward and backward motion parallel to the optical axis of the instrument. The toothed wheels located under the dust covers 110, serve to constrain the motion relative to the table 117 and hence, the patient so that movement occurs only in a specified area.

The vertical positioning element, such as the support shaft 16, raises and lowers the instrument relative to the subject to permit centering of the image in the television picture. The subject is positioned at the table 117 with a table-mounted chin and brow rest of conventional design for positioning and stabilizing the head during the measurement. Inasmuch as this chin and brow rest is of a conventional construction, it is neither illustrated nor described in any further detail herein. However, the base casting 104 is provided with the upstanding handle 114 for manual manipulation by an operator of the apparatus to enable positioning of the instrument with respect to a subject and which is also hereinafter described in more detail.

The beam splitter 34 may be mounted on a base plate 119 of a housing 120 which houses many of the components of the ophthalmic instrument, such as, for example, the television camera 30 the projector lens 24, and condenser lens 22, the slit form 40, the lamp 20 and the mirrors 52 and/or prisms 54. Located beneath the beam splitter 34 is a printed circuit assembly (not shown). This printed circuit assembly may contain the fixation lamp 56. Otherwise, the fixation lamp 56 may be mounted above the beam splitter 34 in the manner as best illustrated in FIGS. 5 and 6 of the drawings. This beam splitter 34 and the fixation target lamp 56 provide a bright target for determining the point of gaze for the subject. The brightness of this target may be controlled to permit persons with low visual acuity to perceive it and to fixate upon it.

In a more preferred embodiment of the invention, the fixation lamp 56 is preferably a light-emitting diode-type lamp and is preferably bi-colored with pulse drive to present a visible pulse stream of alternative colors at about a one second interval rate. The use of this type of fixation lamp 56 and the associated drive provides a wide range of brightness so that the target can be fixated upon by the subject irrespective of visual acuity of the subject. The co-axial location of the fixation target assures maximal ability to accurately reconstruct the three dimensional data. The fixation lamp 56, which causes the iris 84 and the sclera to be illuminated, not only provide for an image of the eye, but also enable an image to be generated for record-keeping purposes.

The normal illumination levels, when slit images are being recorded, is usually inadequate to cause surrounding tissue to be well defined for overall viewing. The common slit lamp camera uses the optical system of the bio-microscope and due to the length of the focal ratio of these systems, a large amount of flash energy is required for exposures. The present invention, however, provides a much more efficient optical design and thus, the illumination energy is reduced by orders of magnitude, when compared to conventional slit lamp photography. The reduction of light energy entering into the eye is, of course, a desirable feature for subject safety and comfort, and also ensures more reliable data.

The operator of the ophthalmic pachymeter will position the half slit images 82, as shown in FIG. 9A, into coincidence so that, in effect, the two half-slit images form somewhat of an "S" shape, as shown in FIG. 9B. This will occur with reference to the fiducial FIG. 110 of FIG. 18, which is displayed for the operator, to thereby align and thereby focus the instrument. The half-slits, as shown, are effectively positioned by the computer in the optical center line of each projector. The operator moves the instrument, preferably by manual manipulation of the handle 114 in order to obtain this coincidence, as hereinafter described, in order to form this S-type image arrangement. When the S-type Tyndall image has been formed of the half Tyndall images, the operator may then take the necessary data.

The motor 36 which moves the slit form 40 will slew the full length slits 26 of FIG. 4 across the eye from each side sequentially to provide the data sequence which will ultimately be stored for analysis. The data is masked by software in order to eliminate extraneous material. The arc of the Tyndall images lies on only one side of the iris section illuminated by the light which is passed through the cornea and has a definable maximum number of pixel loci at the apex from the iris line. The area of the pixel loci is defined by software within the system for each frame and only the data which falls within this defined area is stored for analysis. As a possible exception, a small area at the center which contains the reflection of the fixation lamp may also be stored for compensation of involuntary movements of the eye.

As indicated previously, the operator of the pachymeter can position the half slit images 82. This can be accomplished by manual manipulation of the handle 114 in order to position the television camera 30 in three dimensional space relative to the eye. The desired alignment is obtained by viewing the display before recordation of the data to be analyzed. The generation and positioning of the box, circle or other limiting fiducial marking is by well known computer techniques that are not detailed herein. The operator simply adjusts the controls so that the optical sections coincide at the center of the display monitor. This action assures the operator that the focus and area being measured are correct. The focus and image location are simultaneously adjusted by the operator with reference to the display that shows the image from the camera with the fiducial markings superimposed.

A picture formation of a Tyndall image 82 is generated in the television camera 30. A given point on the Tyndall image 82 is projected onto the photo-sensitive area of the television camera 30. The datum of this given point on the Tyndall image, after an analog-to-digital conversion, represents an X, Y locus with associated brightness. The slit 26 positioned under computer control by the incremental motor 36 is at a known location relative to the optical centerline of the camera 30.

The projector optical axis relating to the camera axis is established in manufacture at a known angular relationship. Since that angle is known, the magnification is known and that the slit position is also known, the angle $\Phi$ is thereby defined in the associated computer software. The height of the datum above the reference plane $\Delta h$ is then calculated. Each raster line intersection with the Tyndall image 82 is used to calculate the associated height value. After the series of images which comprise a complete measurement are so defined and stored in the computer memory, the surface contour for both surfaces of the cornea and the local thickness are displayed for use.

The image which is generated may be identified as either a left eye image or a right eye image by means of a switch (not shown) and which can be located in the instrument base and which is also interfaced to the computer. With this identification, the location of the cursor in the fiducial image 122 is determined in the computer software. A transducer (not shown) may be utilized to provide a signal representative of instrument lateral displacement and is interpreted to determine the eye being examined, due to the fact that the slit lamp 20 is always displaced in the temporal direction for use.

In the preferred embodiment, a point at the vertical center of the cursor in the fiducial FIG. 122 (FIG. 18), displaced a few pixels toward one side, is identified in the software and can serve as a sample for black clamping of the video signal and which is usually accomplished by conventional circuitry. The image of the cornea is located and stored by computer software, based on known characteristics of the corneal image. All initial pixel values for the enclosed line segments of the corneal image, so identified, are averaged for reflected light intensity in terms of pixel brightness and the resultant numerical constant is used to determine the optical character of the remainder of the Tyndall image 62. After determination of the corneal pixel loci, the corneal thickness is derived by known magnification projection angle, surface shape and pixel pitch. The data are then stored by location in an area of the memory for later use.

Referring again to FIG. 7 which indicates a Köhler projector, it can be seen that the image of the slits are brought into focus in the same plane as the television camera 30 by the projection lens 24 and the system of lenses, as previously described. The beam path is folded by mirrors or prisms in order to achieve compact assembly. The focal length of the projection lenses 24 is made to be as long as possible to reduce beam convergence or divergence at the eye which would otherwise degrade the Tyndall image.

In general, the projection lens 24 is selected to provide an aperture sine function on the order of 0.05 or less for best results. The aperture sine is calculated from the optical components by the formula; $f/d^2$ where f is the focal ratio of the lens and d is the distance from the slit to the exit pupil. The brightness of the slit image E is calculated by the formula, $E = (f/d^2)DB$, where D is the optical transmission factor for the lens and B is the luminance of the filament source, e.g. the filament 48. The use of aspheric condenser lenses, optical coatings for all surfaces and a low ratio beam splitter for the fixation target permit the use of lamps in the range of 20 Watts that provide over 400 Lumens as the light source. The minimum brightness level of the slit image reflection is dependent upon the sensitivity of the camera employed. The reflected light is on the order of 4% or less of the incident light and the greater the illumination level of the diffuse reflection, the better the signal to noise ratio of the resultant television signal.

The use of halogen cycle lamps improves the stability of light output with time and provides the best available lamp design. In addition one or more optical filters 190 located on a support pivoted to the housing 120 by a pivot pin 192 and positionable by a handle 94 (FIGS. 5 and 6), or computer controlled mechanism (not illustrated), are included in the illumination path for selected illumination wave band determination. The optical filter 190 also serves to limit energy delivered to the eye 28 to reduce the possibility of phototoxic reaction hazard to the subject. The optical filter 190 would have little or no ultra-violet or infrared transparency.

The image systems of the present invention require extensive depth of focus if both the cornea and the lens of the eye are to be mapped. The fixed focus of the prior art is inadequate for the image quality requisite for good mapping over this large depth. In the present invention, the camera lens is mounted in a mechanical system such as a voice coil 130 which is well known in the art. Alternatively, the projector lens and camera lens may be mounted in such a mechanical system. Referring again to FIG. 17, the camera lens and/or lens 24 are mounted in the center of a cylindrical electro-magnet 132. The electro-magnet 132 is supplied with a current under computer program control which establishes a definable magnetic field strength at any given moment. The action of the electro-magnetic field so generated with the fixed magnetic field of an annular permanent magnet 136 and the restoring force of a spider spring 138 generates a mechanical force balance which tends to displace the coil 132 and attached camera lens along the optical axis of the camera lens.

The magnet 132 and the camera lens and/or lens 24 supported by the spider spring 138 which provides restoring force, as well as confining the motion to a single direction, which is coaxial with the optical axis of the lens. The axial motion is then used under computer control for defining the plane of focus of each of the optical systems for each exposure in the data collection sequence. The optical plane of focus for each of the optical systems is chosen for each slit position and the portion of the eye to be measured in the instant frame to minimize the aberrations due to loss of focus and ray bundle convergence angles. All of these factors are defined in a calibration process and stored as a table or tables of correction data in the computer program.

Imaging Processing and Operation

The following section more specifically describes the process employed in determining thickness and topography of the cornea. However, and while the circuitry as shown in FIG. 22, literally constitutes a part of the apparatus, it is nevertheless described in connection with this image processing and operation, since it is integrally related to the image processing and operation.

In FIG. 20, the relationship between the Tyndall image and the topography of the cornea is shown. Along each raster line in the television display, there is a detectable edge of the Tyndall image which has a virtual image location displaced by delta d ($\Delta$d). This displacement distance is from the point at which the beam would have intersected the optical axis, if undeflected, as best shown in FIG. 15. From this image pixel locus the height of the datum above the reference plane, delta h ($\Delta$h), can be calculated. The calculations are performed for all intercepts in all data frames to provide a matrix of X, Y, Z coordinate loci from which the topography can be plotted.

Referring now to FIG. 21, the voltage waveform produced by the television camera of the instrument is illustrated. The beam is low for black areas 202 and high for brighter areas 204. The brightness amplitude ratio of the anterior edge of the corneal section to the dark pupillary area representing the anterior chamber is used as a reference value for lens reflection assessment. The pixel amplitudes for all elements of the reference areas are averaged to provide the baseline reflectance value.

The television signal voltage wave form, as shown in FIG. 21 is a single raster line of video information in which there are bright areas 208 from the image of the cornea and a brighter image of the iris (represented by the bright areas 204) illuminated by the slit beam after the latter passes through the cornea. A sync pulse signal 212 precedes each line of pictorial information carrying voltage levels. After the sync pulse 212 a short period of a low level blanking pulses 114 follows. The blanking pulse 214 insures that the display is off while the beam is retraced to the start of a new line. The black level, represented by reference numeral 216, is the most negative of the pictorial data voltages in the video composite signal. This level is determined by a keyed clamp circuit of conventional design where a selected spot in the image representing the anterior chamber signal is sampled and used as a minimum brightness determinant. As the voltage increases, the brightness also increases in the displayed image from black to peak white 118 representing saturation of the signal. The voltage level produced at saturation by a "white" image 218 is shown by the dotted line at the top of the illustration. The brightness profile of the corneal image will vary as the local optical density and index of refraction varies.

At the leading edge in time of the Tyndall reflex signal, the signal rises to a peak 219 which represents the cornea to air interface. The amplitude of this signal is quite constant from subject to subject and from time to time. This constant interface signal is used for signal reference against which reflex measurements are made to quantify corneal transparency. Each succeeding raster line will then provide a density profile for a different portion of the cornea.

In the preferred embodiment of the present invention, the optical slit form 40 is moved in small lateral increments by the incremental motor 36 for sequential data sampling. In an alternative embodiment, the optical slit form 40 and incremental motor 36 are replaced by rhonchi rulings of suitable pattern dimension to provide several parallel slit beams in a single exposure. The plural beam system reduces the time required for data acquisition but complicates the computer processing of the data from the Tyndall images. In a further alternative embodiment, the slit 26 can be replaced by a liquid crystal display element so structured as to form electronically selected transparent areas substantially equivalent to the various slit positions in the preferred embodiment of this invention.

Each exposure containing the Tyndall image is converted to digital form by the analog to digital converter 58. Through the action of the data buffer 60, the mode controller 66 the address counter 64 and the digital data memory 62 these sequential amplitude values are stored for use. The data in storage represents the pixel brightness versus locus for each slice of the cornea to be analyzed. Each successive pixel of each successive frame is then multiplied by a constant derived from the cornea to air interface signal average and the optical constant that corrects for the lower normal brightness. As each point is calculated, it is returned to storage in the same sequence for later computation and display. Tyndall illumination provides three-dimensional data sequences of data that are transferred to the computer by the action of the computer interface 58. An area scan using the apparatus of the present invention and the processing time is so small compared to user ability to resolve time that the actual imaging takes place on a real time basis. In other words, analysis and determinations, e.g., optical thickness, are made on a real time basis.

FIG. 22 represents a schematic diagram of part of the electronic circuitry employed in the preferred embodiment of the present invention. The composite video signal from the television camera 30 is applied to the input 220 of a signal conditioning amplifier. The terminated signal is buffered by an emitter follower 222 which drives DC restoration and sync stripper networks 224 and 226. The DC restored and limited video is buffered by a second emitter follower and serves to drive clamping and mixing amplifiers 228 and 230.

A computer derived black reference timing signal 232 is generated in temporal synchronism with the area of the picture from the television camera 30 which defines the pupillary area near the center of the picture. This pulse is conditioned by mono-stable circuits 234 to provide a constant amplitude and constant width sampling pulse. This sampling pulse, via a capacitor 236 allows the capacitor to store a voltage sample of the raw video that represents the "black" level. The black reference level thus generated biases the amplifier 230 for use in the analog to digital converter 58.

Signals from the computer are used for regeneration of the television timing in a conventional integrated circuit device 240 which makes use of a composite sync signal 242 and dot clock signal 244 from the computer display driver. The computer generated fiducial signal 246 and regenerated composite sync are mixed via resistors 248 with the video signal from an emitter follower 250 for providing the monitor signal. The monitor signal is used to drive a conventional CRT display for use as a viewfinder by the user of the pachymeter of the present invention. A potentiometer 252 is provided for setting sync injection amplitude to conform to IRE or SMPTE standards.

The display of the data can take the form of a single frame's information that can be displayed as false colored areas for relative transparency, for example. The entire set of frames may be combined to form a virtual three-dimensional display of surface contour or membrane thickness as needed. The data also may be presented simply as a numerical value for average optical density, density area or other forms that the user finds most useful, by the use of well-known display techniques.

When a suitable image or sequence of images has been stored and the requisite computations performed in the computer, the digital information that defines the cornea can be displayed in some arbitrary color upon the monitor together with the alphanumeric information image from computer by conventional video mixer means. Alternatively the data may be presented for use in any of several formats such as plotted graphs, tabular numerical form, pseudo three dimensional shaded surface plots or other formats that are well known in the art.

Referring again FIG. 4, the motion imparted to the slit form or so-called slit carrier member 40 is controlled by the computer through the action of the incremental stepper motor 36. In an alternative embodiment a second slit 260 of lesser length than the slit 26 is provided in both beam projection paths for the purpose of focusing the instrument. The two half slits so produced are placed by the operator into contact at the point of reflection of the fixation lamp 56 to establish proper alignment prior to recordation of the image sequence.

Thus, there has been illustrated and described a unique and novel ophthalmic pachymeter which enables determination of the thickness and relative optical density of the cornea on a real-time basis and which thereby fulfills all of the objects and advantages which have been sought. It should be understood that many changes, modifications, variations and other uses and applications will become apparent to those skilled in the art after considering this specification and the accompanying drawings. Therefore, any and all such changes, modifications, variations and other uses and applications which do not depart from the spirit and scope of the invention, are deemed to be covered by the invention.

Having thus described the invention, what I desire to claim and secure by letters patent is:

1. An ophthalmic instrument for aiding in determining one or more physical characteristics of the anterior segment of the eye, comprising:
   a) light projector means including a slit means for illuminating a defined area of the cornea;
   b) means for making Scheimpflug corrections with respect to the illuminated area of the cornea to obtain correct plane of focus;
   c) imaging means for providing a television image of selected portions of the illuminated area of the eye as illuminated by the projector means;
   d) means cooperatively located with respect to the projector means for receiving the image of the selected portions of the eye and for generating and transmitting signals representative of the image of the eye in digital format;
   e) analysis means receiving the signals representative of the image for detecting and storing relative brightness levels within the defined area and which brightness levels are directly correlated to the one or more physical characteristics to be determined.

2. The ophthalmic instrument according to claim 1, wherein the means cooperatively located is a video source and that a converter means is provided for converting portions of the video signals into digital format.

3. The ophthalmic instrument according to claim 2, further comprising a means for defining data points based upon relative numerical values detected by the converter means.

4. The ophthalmic instrument according to claim 3, further comprising means responsive to the data points for defining a reference level.

5. The ophthalmic instrument according to claim 4 further comprising means for locating the light projector means relative to the cornea so that the instantaneous position of the slit means constitutes a masking means for delineating a portion of the signal in digital format to define the shape of the cornea.

6. The ophthalmic instrument according to claim 1 wherein said instrument is located with respect to an eye for aiding in determining physical characteristics comprising thickness and surface contour of the anterior segment of the eye, and said analysis means receiving the video signal in digital format and operating in conjunction with a processing means for determining the thickness of the eye anterior segment and the surface contour thereof.

7. An ophthalmic instrument for aiding in determining the thickness and relative optical density of the cornea of an eye on a real-time basis, said instrument comprising:
   a) illumination means for illuminating a pre-selected area of the cornea of the eye in which the digitally encoded images are to be generated;
   b) slit projector means for illuminating a portion of the cornea of the eye;
   c) Scheimpflug correction means associated with said slit projector means for correcting plane of focus;
   d) television means for generating television images of the illuminated area of the cornea;
   e) converter means for converting the television images into digitally encoded images;
   f) processing means for receiving the digitally encoded images from the slit projector means and generating data used in the determination of the thickness and of the optical density of the cornea, said processing means generating the data related to the digitally encoded images at substantially the same time that the digitally encoded television images of the eye are being generated; and
   g) means for generating a display of the thickness and optical density of the eye from the data generated therefor.

8. The ophthalmic instrument according to claim 7 wherein said instrument further comprises:
   a) storage means associated with the processing means for receiving and storing the processed digitally encoded television images in digital format; and
   b) means operatively connected to the storage means for regenerating the images which were stored in the storage means.

9. The ophthalmic instrument according to claim 7 wherein the digitally encoded images are comprised of a plurality of digital data points and the instrument further comprises discriminator means for reducing the number of digital data points in the digitally encoded images processed by the processing means.

10. The ophthalmic instrument according to claim 9 wherein the discriminator means operates in conjunction with the processing means to reduce the number of data points processed to define each significant element on a reflected image of an anterior portion of the eye.

11. The ophthalmic instrument according to claim 7 wherein a voice coil is operatively connected to said slit projector means for moving same to obtain a Scheimpflug correction therefor.

12. A system for producing surface contour maps of the cornea of the eye which includes a projection illumination means for illuminating areas of the cornea for producing a definable spatial delineation of corneal contour, a slit movable across the plane of the cornea, and means for generating images of the illuminated area of the cornea, an improvement compromising means for tilting the plane of the means for generating images or the slit relative to the illuminated area of the eye to obtain a Scheimpflug correction therefor.

13. The system according to claim 12 wherein the means for generating images of the illuminated areas of the cornea further comprises:

a) video signal generating means for rendering the illuminated areas into electrical analog signals; and b) digitizer means for conversion of said analog signals into computer acceptable digital signals.

14. The system according to claim 13 wherein said improvement also comprises computer means for processing the digital signals and generating data to provide a determination of the corneal surface shape from said digital signals and generating control signals for generating a map of the surface contour of the cornea of the eye.

15. The system according to claim 12 wherein the slit is carried in a slit frame and the plane of the slit frame relative to the cornea is adjustable.

16. An ophthalmic instrument for determining physical characteristics of an eye to aid in identifying exact and precise location of optical discontinuities and/or aberrations of the eye, said instrument comprising:

a) a light projector means for illuminating a portion of an eye;

b) electronic imaging means for obtaining electronic signal images of illuminated portions of the eye;

c) slit means optically interposed between the light projector means and the electronic imaging means;

d) means causing relative movement of the slit means relative to the eye to enable a plurality of slit image exposures of the eye during such relative movement and generation of the electronic signal images during such slit image exposures;

e) means for shifting the plane of the slit means to obtain a correct focal plane and correct for parallax; and f) processing means receiving the electronic signals for processing the signals to identify discontinuities and optical aberrations of the eye.

17. The ophthalmic instrument according to claim 16 wherein the electronic imaging means generates electronic analog signals and the instrument comprises a converter means for converting the analog image signals into digital signals for digital processing.

18. The ophthalmic instrument according to claim 17 wherein said instrument comprises a fixation target lamp for enabling fixation of an eye during imaging thereof.

19. The ophthalmic instrument according to claim 16 wherein the means causing relative movement causes movement of the slit means relative to the eye and in relation to the operation of the electronic imaging means.

20. The ophthalmic instrument according to claim 19 wherein the instrument measures elemental brightness of a portion of a Tyndall image of the eye.

21. The ophthalmic instrument according to claim 20 wherein the instrument comprises fiducial means for delineating a portion of the eye to be imaged.

22. A method for ascertaining the extent of an optical aberration or an optical discontinuity of tissue of the eye comprising the steps of:

a) selectively illuminating the tissue area of the eye to be analyzed;

b) moving an optical slit across the plane of the tissue area of the eye to be analyzed;

c) adjusting the plane of the slit to obtain a Scheimpflug correction therefore;

d) receiving and quantifying an image of the said tissue;

e) delineating the portions of the image which contains the optical aberration or optical discontinuity and providing data representative therefor in electronic format; and f) analyzing the relative numerical magnitude of said electronic data to ascertain the severity of the optical aberration or optical discontinuity.

23. The method as recited in claim 22 wherein said method comprises converting said delineated portions into digital data and analyzing the digital data.

24. The method as recited in claim 23 further comprising the steps of establishing threshold values for said digital data, enumerating the data according to relative magnitude and location and converting the enumerated data into an area form.

25. The method as recited in claim 24 further comprising the steps of measuring a locus of data points defined in the image in terms of brightness relative to a second area and multiplying the defined locus of data points by a constant for compensation of optical losses.

* * * * *